(12) United States Patent
Taft et al.

(10) Patent No.: US 10,010,412 B2
(45) Date of Patent: Jul. 3, 2018

(54) CONICAL CRIMPER

(75) Inventors: Rob Taft, Irvine, CA (US); Travis Zenyo Oba, Corona, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 1386 days.

(21) Appl. No.: 13/558,053

(22) Filed: Jul. 25, 2012

(65) Prior Publication Data
US 2013/0030418 A1 Jan. 31, 2013

Related U.S. Application Data

(60) Provisional application No. 61/512,267, filed on Jul. 27, 2011.

(51) Int. Cl.
| | | |
|---|---|---|
| *B23Q 1/00* | (2006.01) | |
| *A61F 2/24* | (2006.01) | |
| *A61F 2/95* | (2013.01) | |
| *A61F 2/958* | (2013.01) | |

(52) U.S. Cl.
CPC .......... *A61F 2/2418* (2013.01); *A61F 2/2433* (2013.01); *A61F 2/958* (2013.01); *A61F 2002/9522* (2013.01); *A61F 2230/005* (2013.01); *A61F 2230/0054* (2013.01); *A61F 2230/0065* (2013.01); *A61F 2230/0067* (2013.01)

(58) Field of Classification Search
CPC .................. A61F 2002/9522; Y10T 29/53996
USPC ........................................................ 29/283.5
See application file for complete search history.

(56) References Cited

U.S. PATENT DOCUMENTS

| | | | | |
|---|---|---|---|---|
| 1,438,681 A | | 12/1922 | Bath | |
| 1,493,515 A | * | 5/1924 | Berthold | 72/402 |
| 2,079,498 A | * | 5/1937 | Douglas | 72/402 |

(Continued)

FOREIGN PATENT DOCUMENTS

| | | |
|---|---|---|
| DE | 9034 C | 3/1880 |
| WO | 1994014573 A1 | 7/1994 |
| WO | WO-03/047468 A1 | 6/2003 |

OTHER PUBLICATIONS

International Search Report, Nov. 16, 2012.
(Continued)

*Primary Examiner* — Lee D Wilson
(74) *Attorney, Agent, or Firm* — Klarquist Sparkman, LLP; AnneMarie Kaiser

(57) ABSTRACT

Embodiments of crimping devices for crimping stented prosthetic valves and other medical devices from a larger, expanded diameter to a smaller, crimped diameter are disclosed. Some crimping devices utilize a conical surface extending out-of-plane from the direction of crimping, where motion of the conical surface in the out-of-plane direction causes in-plane radially crimping. Other crimping devices comprise a funnel-shaped rigid body having a tapered inner lumen that compresses a medical device moving therethrough. Some funnel-shaped embodiments have slotted sides that allow portions of the medical device to project therethrough. Other funnel-shaped embodiments are used with a tubular sock to pull the medical device through the tapered lumen. Other crimping devices utilize rotating rollers that compress a medical device while the medical device spins between the rollers.

16 Claims, 21 Drawing Sheets

(56) References Cited

U.S. PATENT DOCUMENTS

| | | | | |
|---|---|---|---|---|
| 2,664,996 | A | 1/1954 | Andrews | |
| 2,787,925 | A * | 4/1957 | Buchanan et al. | 72/402 |
| 2,974,367 | A * | 3/1961 | Doering et al. | 425/392 |
| 2,986,192 | A * | 5/1961 | Macleod | 29/819 |
| 3,154,978 | A | 11/1964 | Baker | |
| 3,307,451 | A | 3/1967 | Schuetz | |
| 3,417,598 | A | 12/1968 | Valente | |
| 3,695,087 | A | 10/1972 | Tuberman | |
| 3,849,858 | A * | 11/1974 | Whitledge et al. | 29/237 |
| 4,308,744 | A | 1/1982 | Baker | |
| 4,350,036 | A | 9/1982 | Valente | |
| 4,454,657 | A | 6/1984 | Yasumi | |
| 4,575,917 | A * | 3/1986 | Kana et al. | 29/520 |
| 4,578,982 | A | 4/1986 | Schrock | |
| 5,261,263 | A | 11/1993 | Whitesell | |
| 5,411,521 | A | 5/1995 | Putnam et al. | |
| 5,437,083 | A | 8/1995 | Williams et al. | |
| 5,626,604 | A | 5/1997 | Cottone, Jr. | |
| 5,749,921 | A | 5/1998 | Lenker et al. | |
| 5,810,873 | A | 9/1998 | Morales | |
| 5,824,041 | A * | 10/1998 | Lenker | A61F 2/91 |
| | | | | 606/195 |
| 5,836,952 | A | 11/1998 | Davis et al. | |
| 5,893,852 | A | 4/1999 | Morales | |
| 5,913,871 | A | 6/1999 | Werneth et al. | |
| 5,918,511 | A | 7/1999 | Sabbaghian et al. | |
| 5,951,540 | A | 9/1999 | Verbeek | |
| 5,992,000 | A * | 11/1999 | Humphrey et al. | 29/516 |
| 6,007,543 | A | 12/1999 | Ellis et al. | |
| 6,009,614 | A | 1/2000 | Morales | |
| 6,051,002 | A | 4/2000 | Morales | |
| 6,074,381 | A | 6/2000 | Dinh et al. | |
| 6,082,990 | A | 7/2000 | Jackson et al. | |
| 6,125,523 | A | 10/2000 | Brown et al. | |
| 6,167,605 | B1 * | 1/2001 | Morales | 29/282 |
| 6,176,116 | B1 | 1/2001 | Wilhelm et al. | |
| 6,309,383 | B1 | 10/2001 | Campbell et al. | |
| 6,352,547 | B1 | 3/2002 | Brown et al. | |
| 6,360,577 | B2 * | 3/2002 | Austin | 72/402 |
| 6,364,870 | B1 | 4/2002 | Pinchasik | |
| 6,387,117 | B1 | 5/2002 | Arnold, Jr. et al. | |
| 6,558,418 | B2 | 5/2003 | Carpentier et al. | |
| 6,568,235 | B1 * | 5/2003 | Kokish | 72/402 |
| 6,618,921 | B1 | 9/2003 | Thornton | |
| 6,629,350 | B2 * | 10/2003 | Motsenbocker | 29/283.5 |
| 6,648,901 | B2 * | 11/2003 | Fleischman | A61B 17/11 |
| | | | | 606/155 |
| 6,651,478 | B1 * | 11/2003 | Kokish | 72/402 |
| 6,682,553 | B1 | 1/2004 | Webler, Jr. | |
| 6,730,118 | B2 | 5/2004 | Spenser et al. | |
| 6,769,161 | B2 | 8/2004 | Brown et al. | |
| 6,823,576 | B2 * | 11/2004 | Austin | 29/516 |
| 6,840,081 | B2 * | 1/2005 | Kokish | 72/402 |
| 6,889,579 | B1 * | 5/2005 | Brown | 81/90.2 |
| 6,915,560 | B2 * | 7/2005 | Austin | 29/722 |
| 6,920,674 | B2 | 7/2005 | Thornton | |
| 6,925,847 | B2 * | 8/2005 | Motsenbocker | 72/402 |
| 6,926,732 | B2 * | 8/2005 | Derus | A61F 2/95 |
| | | | | 623/1.11 |
| 6,931,899 | B2 | 8/2005 | Goff et al. | |
| 6,968,607 | B2 * | 11/2005 | Motsenbocker | 29/505 |
| 6,988,881 | B2 * | 1/2006 | Motsenbocker et al. | 425/392 |
| 7,010,953 | B2 | 3/2006 | Stupecky | |
| 7,021,114 | B2 * | 4/2006 | Perreault | 72/402 |
| 7,069,794 | B2 * | 7/2006 | Motsenbocker et al. | 73/862.041 |
| 7,096,554 | B2 * | 8/2006 | Austin et al. | 29/282 |
| 7,143,625 | B2 * | 12/2006 | Edin | 72/402 |
| 7,152,452 | B2 * | 12/2006 | Kokish | A61F 2/958 |
| | | | | 29/282 |
| 7,207,204 | B2 * | 4/2007 | Weber et al. | 72/402 |
| 7,225,518 | B2 * | 6/2007 | Eidenschink et al. | 29/283.5 |
| 7,229,405 | B2 * | 6/2007 | Lau | A61B 17/00234 |
| | | | | 600/37 |
| 7,284,401 | B2 * | 10/2007 | Larson | A61F 2/95 |
| | | | | 72/402 |
| 7,389,670 | B1 * | 6/2008 | Kokish | A61F 2/95 |
| | | | | 72/402 |
| 7,415,861 | B2 * | 8/2008 | Sokel | A61F 2/2415 |
| | | | | 29/283.5 |
| 7,487,579 | B2 | 2/2009 | Eidenschink et al. | |
| 7,530,253 | B2 * | 5/2009 | Spenser et al. | 72/402 |
| 7,587,801 | B2 * | 9/2009 | Austin | 29/283.5 |
| 7,611,535 | B2 * | 11/2009 | Woolfson | A61F 2/2409 |
| | | | | 623/1.36 |
| 7,628,051 | B1 | 12/2009 | Kokish et al. | |
| 7,886,661 | B1 * | 2/2011 | Goff | B21J 9/06 |
| | | | | 100/232 |
| 7,892,201 | B1 | 2/2011 | Laguna et al. | |
| 7,895,876 | B2 * | 3/2011 | Spenser et al. | 72/402 |
| 7,922,755 | B2 * | 4/2011 | Acosta | A61F 2/91 |
| | | | | 623/1.11 |
| 7,963,142 | B2 * | 6/2011 | Goff | A61F 2/95 |
| | | | | 29/282 |
| 7,967,138 | B2 | 6/2011 | Ryan et al. | |
| 7,992,273 | B2 * | 8/2011 | Austin | 29/283.5 |
| 8,006,535 | B2 * | 8/2011 | Righini et al. | 72/402 |
| 8,112,857 | B2 | 2/2012 | Voelkl | |
| 8,141,226 | B2 * | 3/2012 | Seyler et al. | 29/508 |
| 8,216,295 | B2 * | 7/2012 | Benjamin | A61F 2/95 |
| | | | | 623/1.11 |
| 8,220,307 | B2 * | 7/2012 | Goff | B21D 41/04 |
| | | | | 29/282 |
| 8,312,614 | B2 * | 11/2012 | Sokel | 29/515 |
| 8,468,667 | B2 * | 6/2013 | Straubinger | A61F 2/2427 |
| | | | | 29/237 |
| 8,533,925 | B2 * | 9/2013 | Austin | 29/447 |
| 8,591,566 | B2 * | 11/2013 | Newell | A61F 2/82 |
| | | | | 623/1.11 |
| 8,667,668 | B2 * | 3/2014 | Seyler et al. | 29/728 |
| 8,721,714 | B2 * | 5/2014 | Kelley | A61F 2/2436 |
| | | | | 623/2.11 |
| 8,747,448 | B2 * | 6/2014 | Argentine | A61F 2/95 |
| | | | | 623/1.11 |
| 9,326,876 | B2 * | 5/2016 | Acosta | A61F 2/966 |
| 2002/0035774 | A1 * | 3/2002 | Austin | 29/516 |
| 2002/0138966 | A1 * | 10/2002 | Motsenbocker | 29/516 |
| 2003/0032975 | A1 * | 2/2003 | Bonutti | A61B 17/0218 |
| | | | | 606/192 |
| 2003/0192164 | A1 * | 10/2003 | Austin | 29/505 |
| 2005/0085890 | A1 * | 4/2005 | Rasmussen | A61F 2/95 |
| | | | | 623/1.11 |
| 2005/0183259 | A1 * | 8/2005 | Eidenschink et al. | 29/508 |
| 2005/0229670 | A1 * | 10/2005 | Perreault | A61F 2/958 |
| | | | | 72/402 |
| 2006/0213049 | A1 * | 9/2006 | Serrano et al. | 29/508 |
| 2007/0056346 | A1 | 3/2007 | Spenser et al. | |
| 2007/0061009 | A1 | 3/2007 | Spenser et al. | |
| 2007/0239271 | A1 * | 10/2007 | Nguyen | A61F 2/2436 |
| | | | | 623/2.11 |
| 2008/0255653 | A1 * | 10/2008 | Schkolnik | A61F 2/95 |
| | | | | 623/1.11 |
| 2009/0043249 | A1 | 2/2009 | Sokel | |
| 2010/0154195 | A1 * | 6/2010 | Austin | 29/515 |
| 2010/0292780 | A1 | 11/2010 | Straubinger et al. | |
| 2012/0239142 | A1 | 9/2012 | Liu et al. | |
| 2013/0283596 | A1 * | 10/2013 | Golan et al. | 29/505 |
| 2014/0012372 | A1 * | 1/2014 | Chau et al. | 623/2.18 |
| 2014/0144000 | A1 * | 5/2014 | Creaven et al. | 29/505 |
| 2014/0260097 | A1 * | 9/2014 | Avery et al. | 53/428 |
| 2015/0007630 | A1 * | 1/2015 | Maimon et al. | 72/370.25 |

OTHER PUBLICATIONS http://www.machinesolutions.org/custom.sub.--tools.sub.--equipment/HV200.h-tm, 2 pages, Aug. 22, 2006.

http://www.machinesolutions.org/custom.sub.--tools.sub.--equipment/HV200.s-ub.--specs.htm, 1 page, Aug. 22, 2006.

* cited by examiner

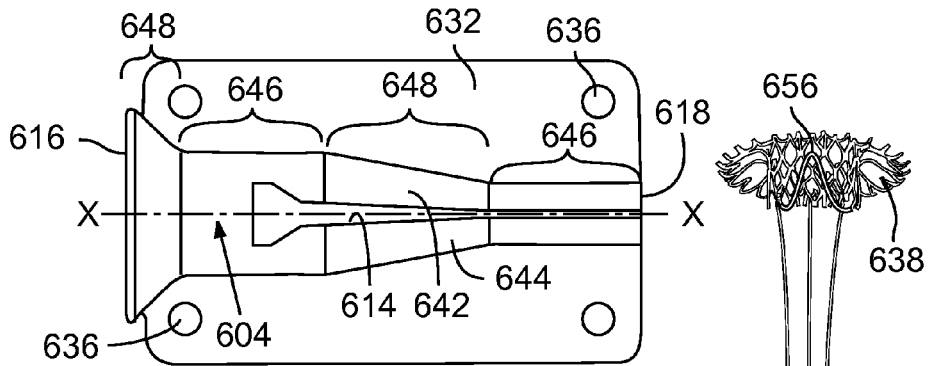
FIG. 10
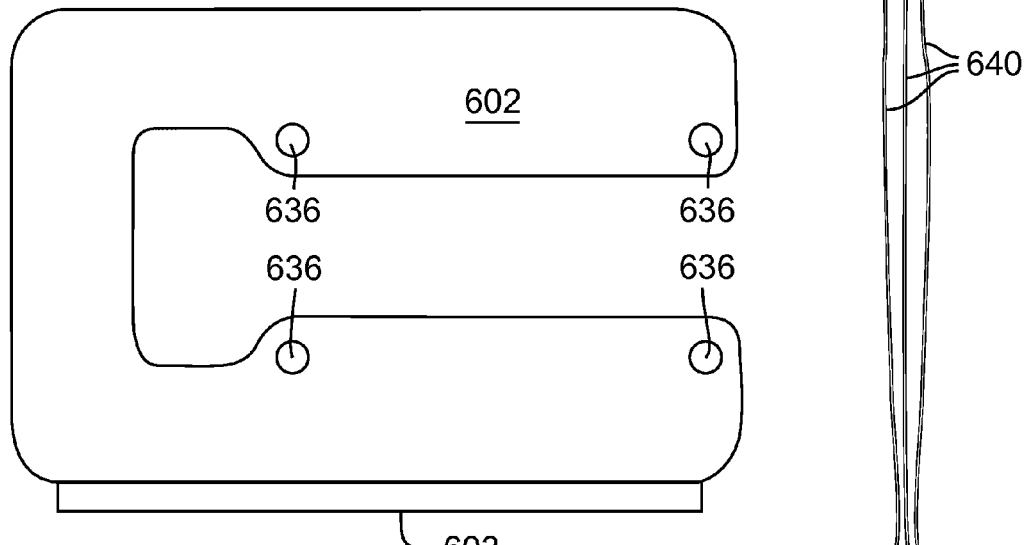
FIG. 11
FIG. 13
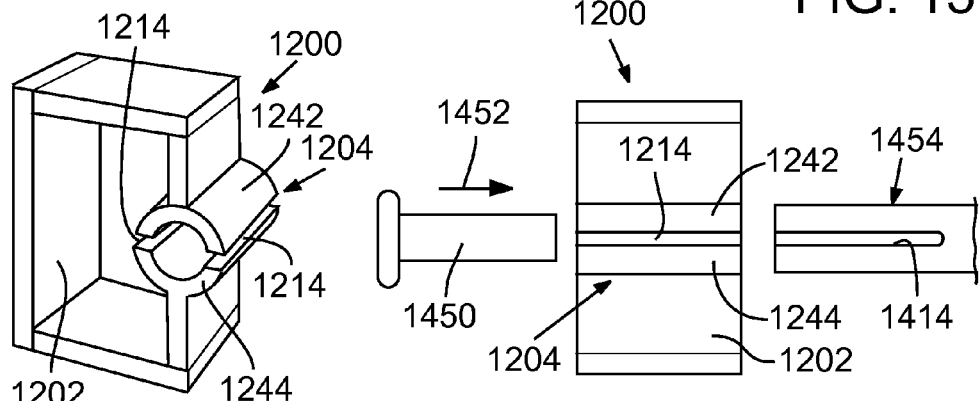
FIG. 12
FIG. 14

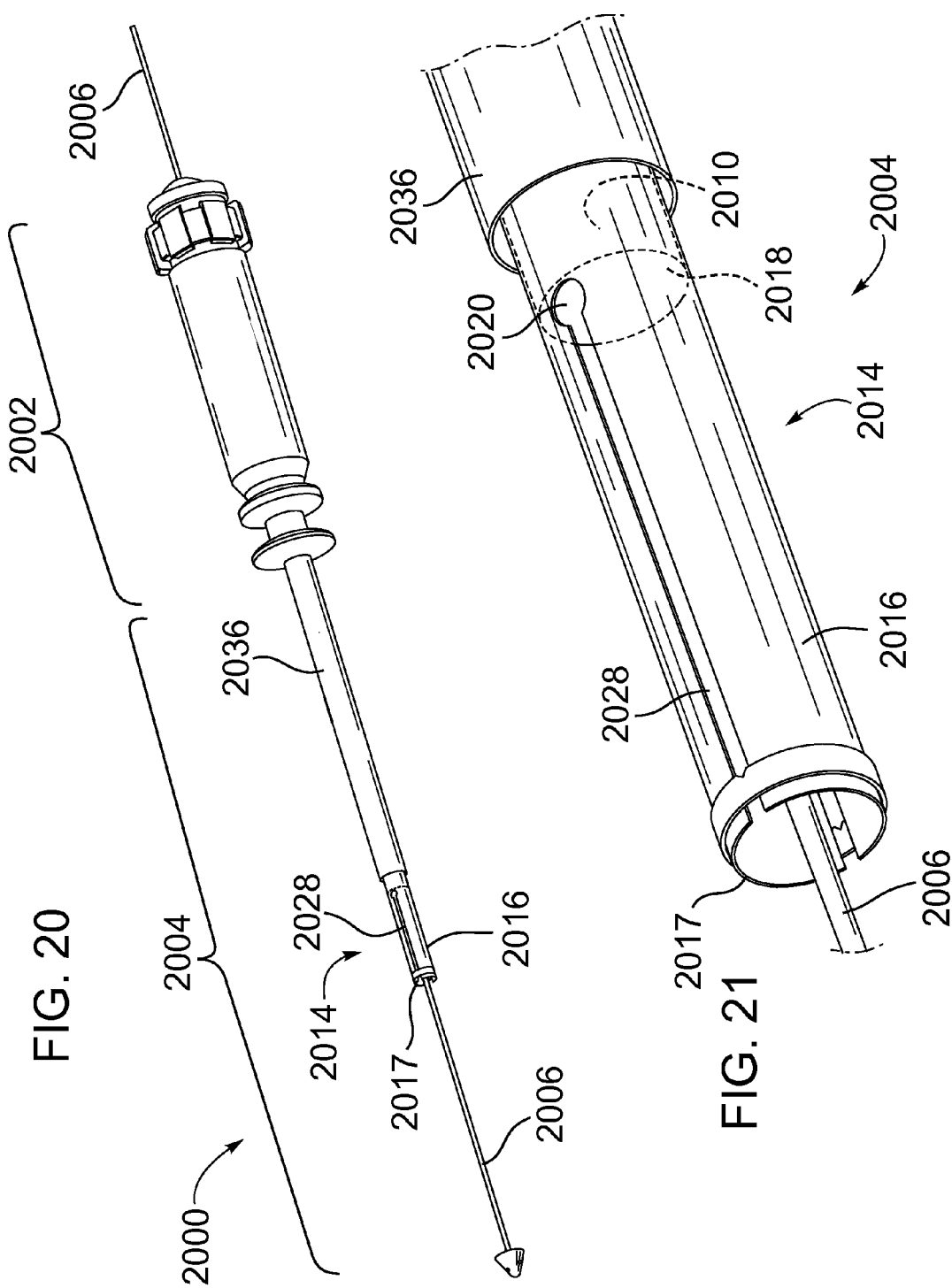

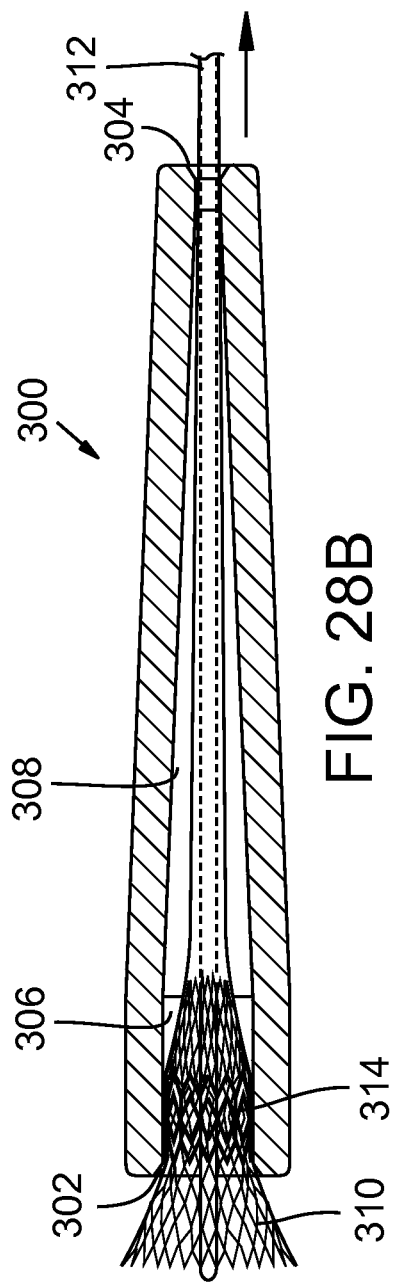
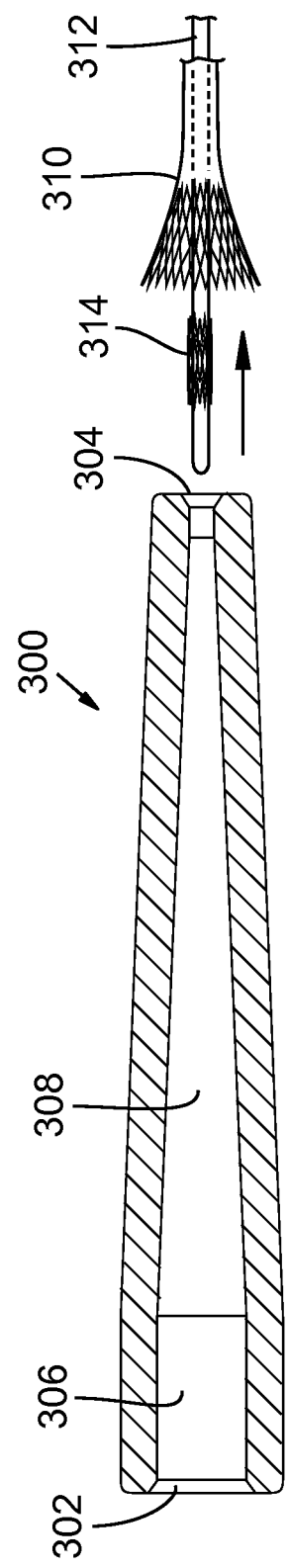
FIG. 28B
FIG. 28C

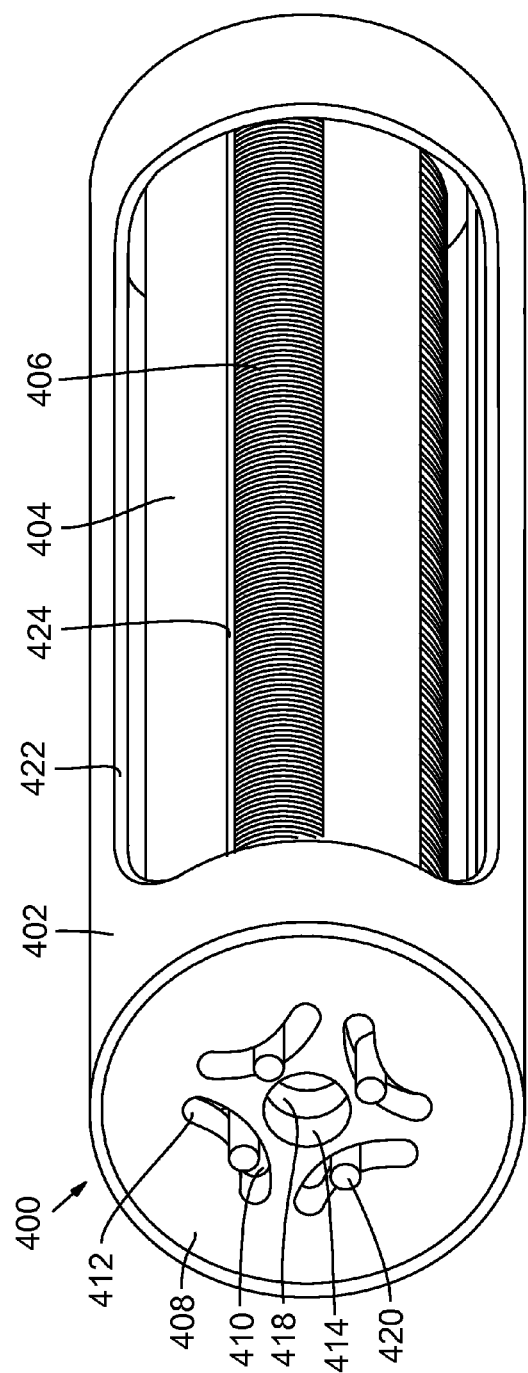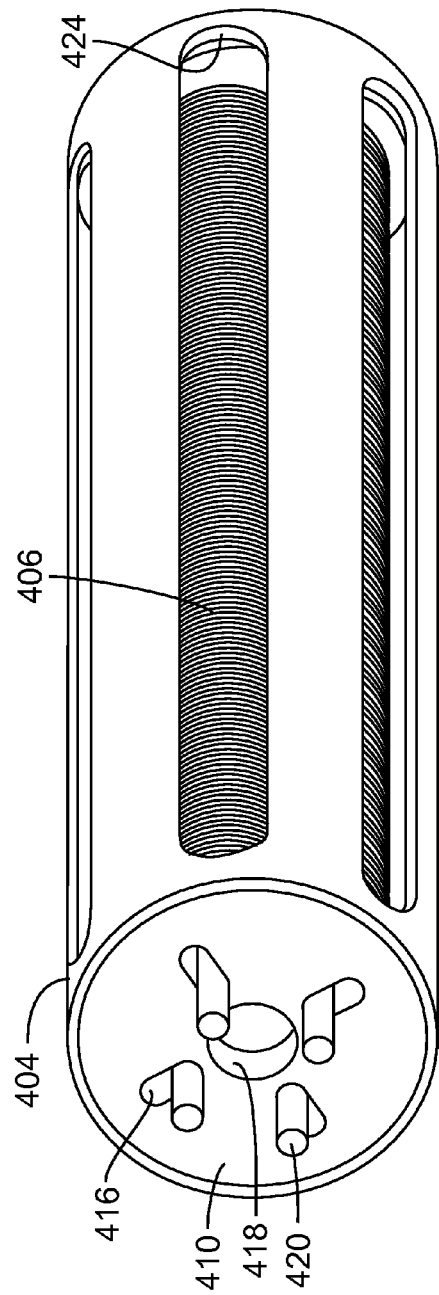

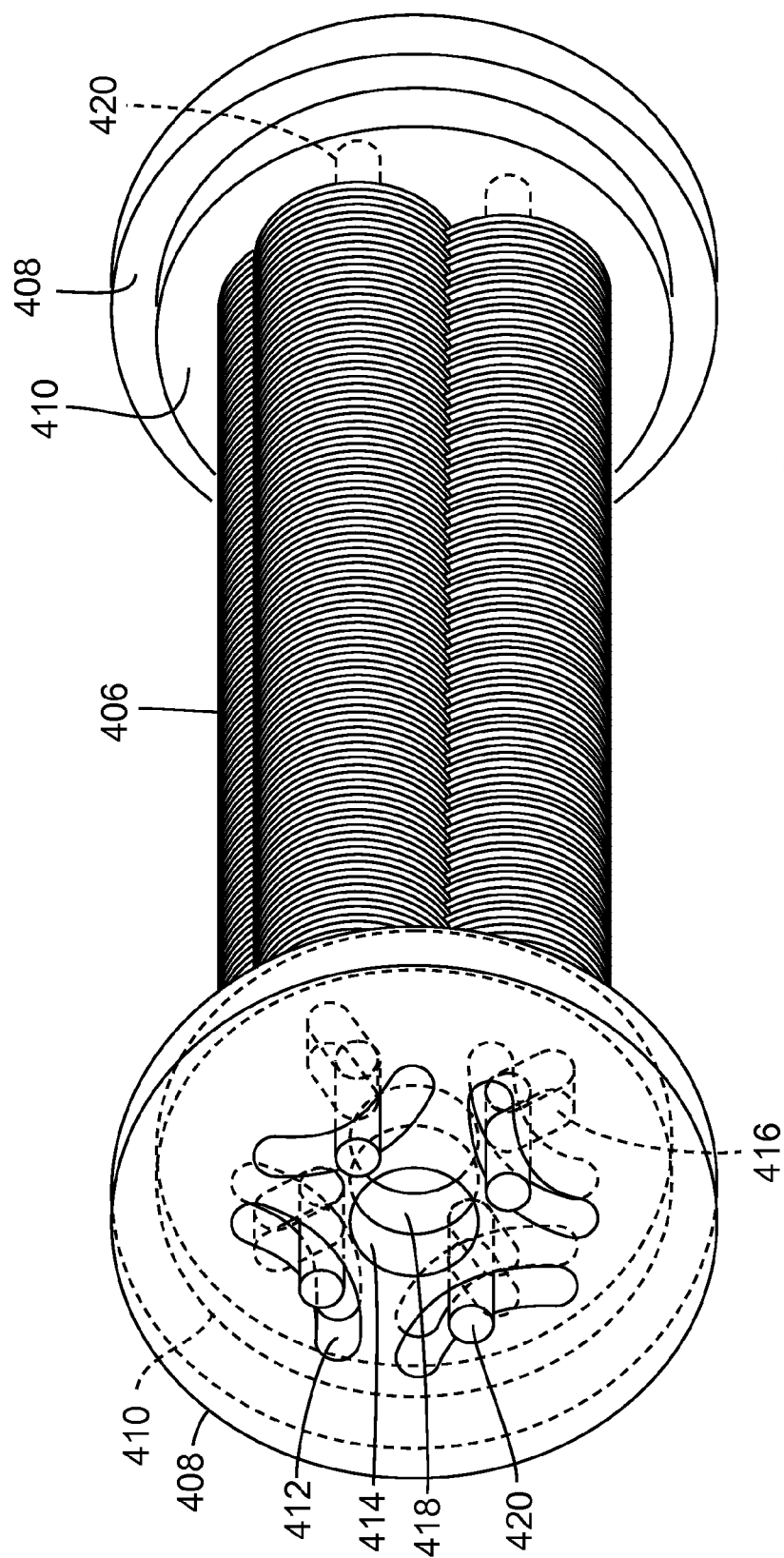

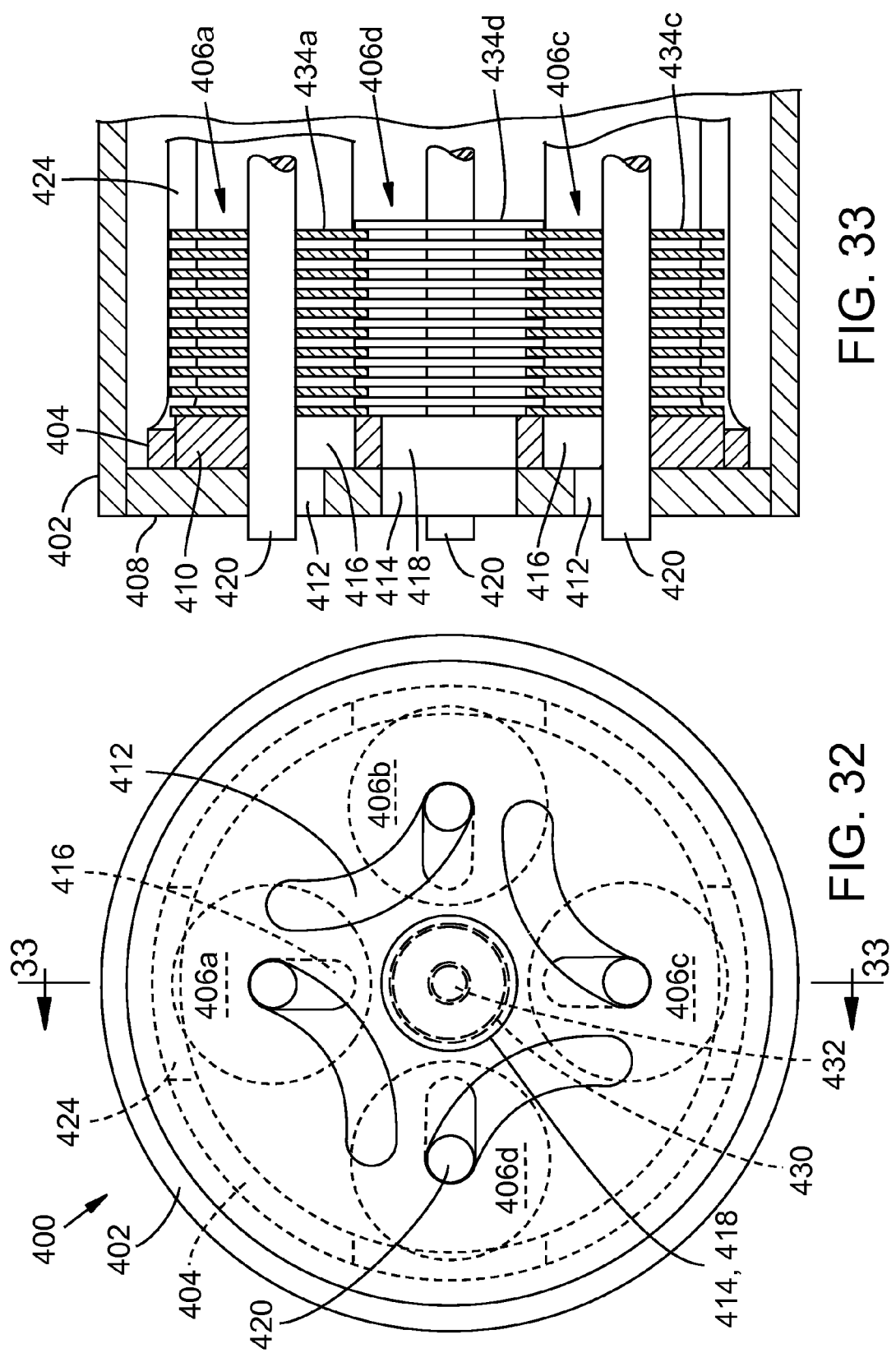

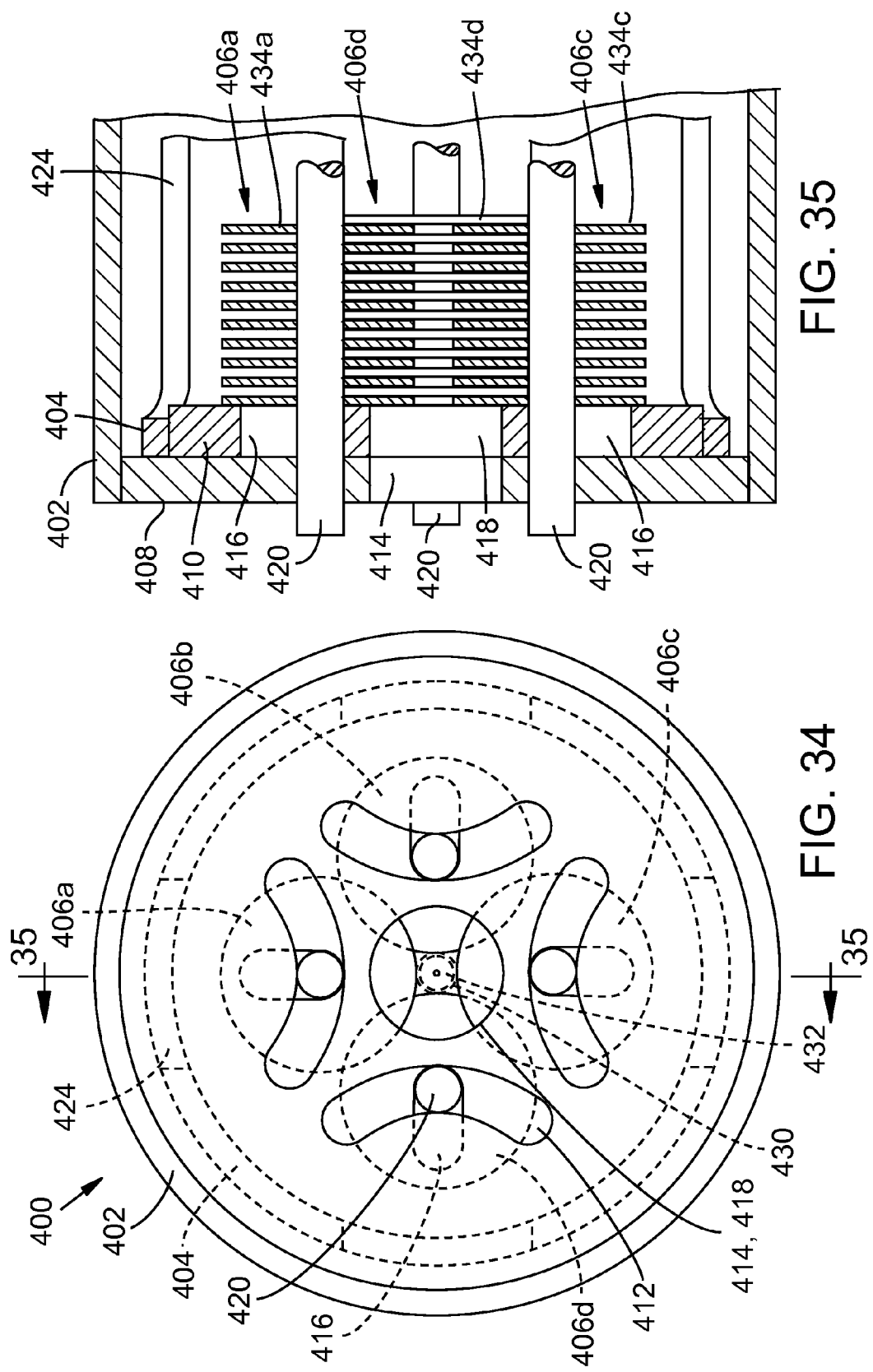

CONICAL CRIMPER

CROSS REFERENCE TO RELATED APPLICATION

This application claims the benefit of U.S. Provisional Patent Application No. 61/512,267, filed Jul. 27, 2011, which is incorporated by reference herein.

FIELD

The present disclosure relates to crimping devices for crimping stents, frames, stented prosthetic valves, and other medical devices from a larger, expanded diameter to a smaller, crimped diameter.

BACKGROUND

A stent is a generally cylindrical prosthesis introduced into a lumen of a body vessel via a catheterization technique. Stents may be self-expanding or balloon expandable. Stents are typically crimped from an initial relatively large (or expanded) diameter to a smaller, crimped diameter prior to advancement to a treatment site in the body. Before crimping, a balloon-expandable stent is typically placed over an expandable balloon on a catheter shaft. In cases where the stent was manufactured in its fully crimped diameter, the stent is often expanded and then crimped on the balloon. A crimping device, or crimper, is used to crimp the stent to its crimped diameter for delivery.

In recent years, a variety of prosthetic valves have been developed wherein a valve structure is mounted on a stent and then delivered to a treatment site via a percutaneous catheterization technique. Prosthetic valves are typically much larger in diameter relative to coronary stents. For example, a typical coronary stent diameter is only 1.5 to 4.0 mm in its expanded size, while a stented prosthetic valve diameter will typically be in the range of about 19 to 29 mm, at least 5 times as large as a coronary stent. In another difference, coronary stents are stand-alone devices while, for prosthetic valves, the stent functions as a scaffold to hold the valve structure. The valve structure is typically made of biological materials such as pericardium valves or harvested valves. For improved function after deployment, it is often desirable to package and store such valves in the open (i.e., expanded) diameter inside a preserving solution up until the time the valve is mounted on a delivery device for implantation. Using this procedure, it may be necessary to crimp the valve in the operation room a few minutes before implantation, therefore precluding pre-crimping by the manufacturer. Thus many crimping devices are now shipped as a disposable accessory along with the valve and delivery system, thus increasing the importance of portability of such crimping devices.

Generally, conventional crimping devices operate by one of two methods. In one method, a stent is driven through a cone-like surface, which compresses the stent to a smaller diameter. For example, a static conical tube can be passed over a stent, thereby reducing its diameter. While this method can be effective for some stents formed from easily deformable materials (e.g., Nitinol), it is less effective for stents formed from more rigid or stiffer materials. Furthermore, even for stents formed from easily deformable materials, the design of the stent can sometimes prohibit the use of a static conical tube for crimping. For example, strut thickness and other design features of the frame can create a high radial force which would prohibit the use of a static conical tube.

The second method uses crimping jaws to create a cylinder-like surface that can change diameter. This method is effective for stents formed of both easily deformable materials as well as less deformable materials. One example of such a crimping device is disclosed in U.S. Pat. No. 7,530,253 (hereafter "the '253 patent"), which is incorporated herein by reference. The device disclosed in the '253 patent uses a spiral track positioned around the jaws to drive the crimping jaws in a radial direction, thus operating in the plane of crimping. The device of the '253 patent, however, has limited portability, due to increases in its size and weight when designed for stents of over 29 mm expanded diameter.

Other conventional devices having crimping jaws use, for example, sloped grooves in the plane of crimping to drive the jaws, or rotational motion within the plane of crimping. Such devices with mechanisms within the plane of motion can disadvantageously be limited in terms of size, weight, crimping strength, mechanical advantage, and control of the crimping process. Additionally, newer medical devices sometimes contain components or features that are not designed to be crimped. Conventional crimping devices cannot accommodate such medical devices, because the crimping devices are simply designed to crimp the entire medical device. There thus remains a need for an improved crimping device that addresses these and other disadvantages in the prior art and that has improved portability and a simplified design.

SUMMARY

Embodiments of crimpers, or crimping devices, are disclosed herein. Some embodiments include an array of crimping jaws that radially compress an object and are driven by a mechanism out of plane with the plane of crimping. For example, the crimping jaws can be driven by axial motion that is perpendicular to the plane of crimping. Disclosed crimping devices include a central iris of variable size that can be used to crimp medical or other devices (e.g., reduce the diameter of a radially compressible medical device) or otherwise grip or hold an object in place.

In one embodiment, a crimping device can include a plurality of crimping jaws secured to an outer annular frame positioned adjacent an external surface of an inner annular frame. The crimping jaws can extend into the inner frame and come together near the middle of the inner frame to surround a stent, stented prosthetic valve, or other expandable medical device positioned within the central area of the inner frame, with the longitudinal axis of the stent parallel to the longitudinal axis of the inner frame. Movement of the inner frame with respect to the outer frame along the longitudinal axis of the stent (e.g., perpendicular to the plane of crimping) can cause the crimping jaws to move closer together, thereby reducing the diameter of the stent (e.g., crimping the stent in the radial direction). Such a crimping device can be configured to allow access to the medical device while it is being crimped, thus ensuring proper positioning or alignment within the crimping device, which can be important for medical devices having components that are not crimped.

In other embodiments, other out-of-plane surfaces can be utilized to actuate or drive the crimping jaws closer together, rather than the outer surface of an inner frame driving motion of the crimping jaws. For example, in one embodiment, a plurality of sloped guiderails and bearings can drive the motion of the crimping jaws. The sloped guiderails can be arranged to form a conical shape, with a guiderail provided for each of the crimping jaws. A bearing positioned within the crimping jaw can allow for smooth motion of the guiderails through the crimping jaws. As the crimping jaws are moved along the sloped guiderails (e.g., in a longitudinal direction), the jaws can move closer together, thereby being configured to crimp a medical or other device in the radial direction (e.g., out of plane with the motion along the guiderails).

Other embodiments of crimping devices disclosed herein include a funnel-shaped rigid body having a split or opening between an upper and a lower half of the funnel. For example, in one embodiment, a medical device can be crimped by being moved through the split funnel from a first, larger end, towards a second, smaller end. In one example, sutures coupled to the medical device can be used to pull the medical device through the split funnel. The split funnel can be configured such that at least a portion of its length includes a longitudinal slot, allowing non-crimped components of the medical device to extend through the slots. In this manner, a split funnel crimping device can crimp the main body of a medical device while allowing some components, such as anchors, to remain in their original configuration. A transport system with longitudinal slots can be used to transport the crimped medical device from the crimping device to a delivery catheter for implantation within a patient.

Other exemplary crimping systems disclosed herein comprise a funnel-shaped rigid body and a tubular sock. A medical device is placed within the sock and both are pulled through the funnel-shaped device to cause the medical device to be crimped. Optionally, a catheter or other shaft can be positioned within the medical device and the sock such that the medical device is crimped onto the catheter as both are pulled through the funnel.

Another exemplary crimping device disclosed herein comprises a plurality of rotating parallel rollers that are forced radially inwardly toward a medical device to crimp the medical device while the medical device is caused to spin by the rotation of the rollers. The device can include and outer shell and an inner shell with in the outer shell and surrounding the rollers. Relative rotation between the inner and outer shells causes the rollers to move radially. The device comprises inner and outer end plates at each end, the inner end plates fixed to the inner shell and the outer end plates fixed to the outer shell. The outer end plates can be parallel and adjacent to each other on each end of the device. One of the end plates comprises radial slots and the other end plate comprises sloped slots. The rollers each comprise a center pin with plural disks mounted thereon and spaced apart by gaps about the same width as the disks. The ends of each pin extend through the radial slots and the sloped slots. Relative rotation of the inner end plate and the outer end plate causes the pins to move along the slots and causes the rollers to move radially inwardly or outwardly to crimp a medical device. The rollers are also caused to rotate while they are moving radially inwardly such that the medical device spins while it is being crimped.

The foregoing and other features and advantages of the invention will become more apparent from the following detailed description, which proceeds with reference to the accompanying figures.

BRIEF DESCRIPTION OF THE DRAWINGS

FIG. 10 shows a side elevation view of the funnel of the crimping device of FIG. 6.

FIG. 11 shows the stand of the crimping device of FIG. 6.

FIG. 12 shows a schematic view of one embodiment of a transport device for transporting a medical device crimped in the crimping devices according to the present disclosure.

FIG. 13 shows one example of a medical device with sutures to aid in guiding the medical device through a crimping device.

FIG. 14 shows a schematic view of one embodiment of a pushing tool, transport device, and delivery system.

FIG. 20 shows an exemplary embodiment of a delivery system for delivering and implanting a prosthetic valve at a native mitral valve region of the heart.

FIG. 21 is a detailed view of the distal portion of the delivery system of FIG. 20.

FIG. 28B is a cross-sectional side view of the crimping device of FIG. 28A with the stent positioned between the catheter and the stent within a cylindrical portion of the crimping device.

FIG. 28C is a cross-sectional side view of the crimping device of FIG. 28A with the stent crimped onto the catheter after having passes through the crimping device.

FIG. 29 is a perspective view of another exemplary crimping device.

FIG. 30 is a perspective view of the crimping device of FIG. 29 with an outer shell removed.

FIG. 31 is a perspective view of the crimping device of FIG. 29 with both an outer shell and an inner shell removed.

FIG. 32 is an end view of the crimping device of FIG. 29 in a radially expanded state.

FIG. 33 is a cross-sectional side view of a portion of the crimping device of FIG. 29 in the radially expanded state.

FIG. 34 is an end view of the crimping device of FIG. 29 in a radially contracted state.

FIG. 35 is a cross-sectional side view of a portion of the crimping device of FIG. 29 in the radially contracted state.

DETAILED DESCRIPTION

As used in this application and in the claims, the singular forms "a," "an," and "the" include the plural forms unless the context clearly dictates otherwise. Additionally, the term "includes" means "comprises." Although the operations of exemplary embodiments of the disclosed method may be described in a particular, sequential order for convenient presentation, it should be understood that the disclosed embodiments can encompass an order of operations other than the particular, sequential order disclosed. For example, operations described sequentially may in some cases be rearranged or performed concurrently. Further, descriptions and disclosures provided in association with one particular embodiment are not limited to that embodiment, and may be applied to any embodiment disclosed herein. Moreover, for the sake of simplicity, the attached figures may not show the various ways in which the disclosed system, method, and apparatus can be used in combination with other systems, methods, and apparatuses.

FIGS. 1-5 show one embodiment of a crimper, or crimping device, 100 that can be used to crimp (e.g., reduce the diameter of) a medical device, such as a stent, frame, or prosthetic valve, or a similar object. Unless otherwise stated, the terms stent, frame, prosthetic valve, and similar terms are used interchangeably herein to refer to all types of medical devices that can be crimped. The crimping device 100 can be used to crimp a medical device from a larger, expanded diameter, to a smaller, crimped diameter suitable for delivery to a treatment site within a patient (e.g., via percutaneous delivery).

Figure 1:
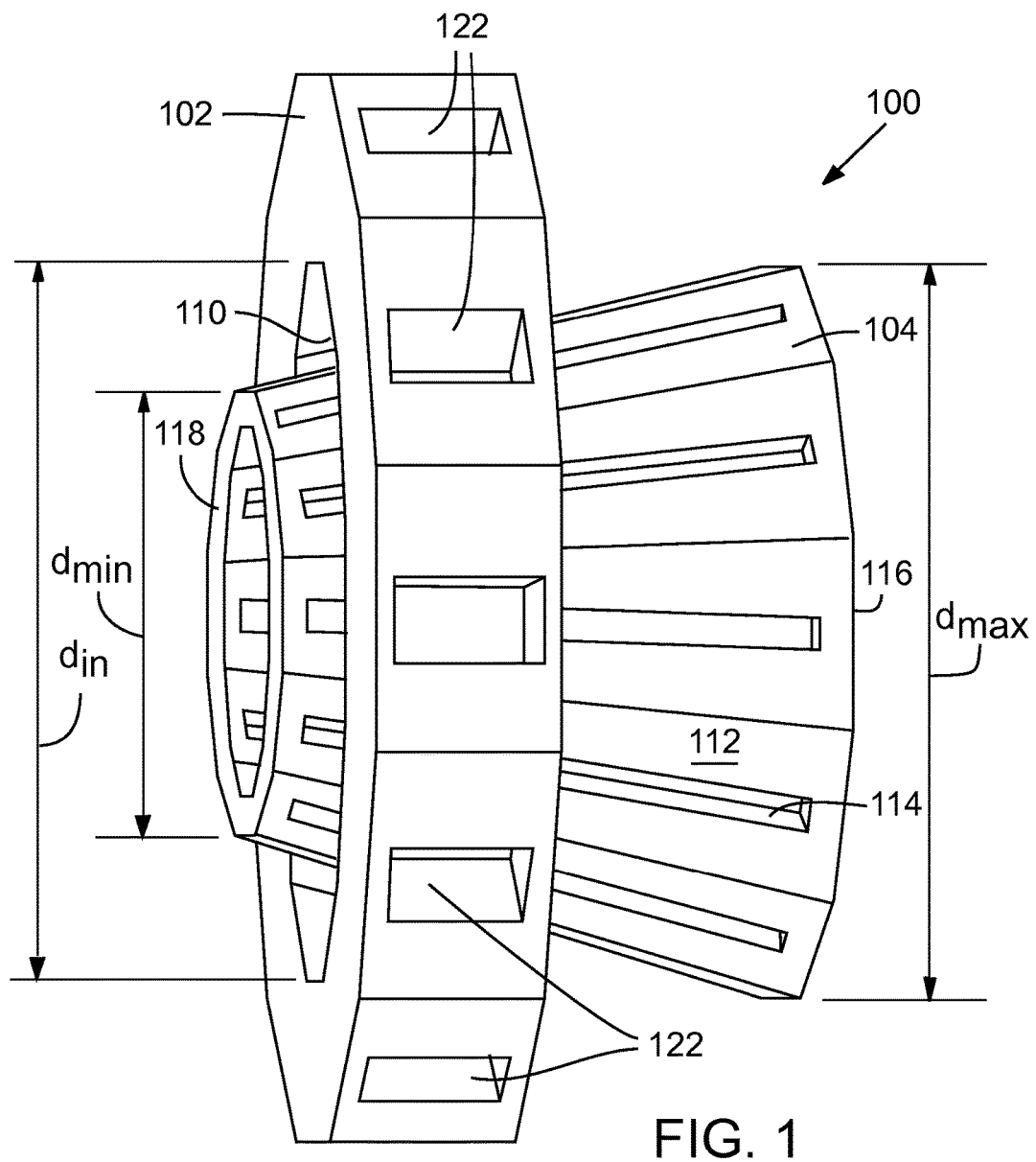
FIG. 1 shows a perspective view of one embodiment of a crimper according to the present disclosure.
Figure 2:
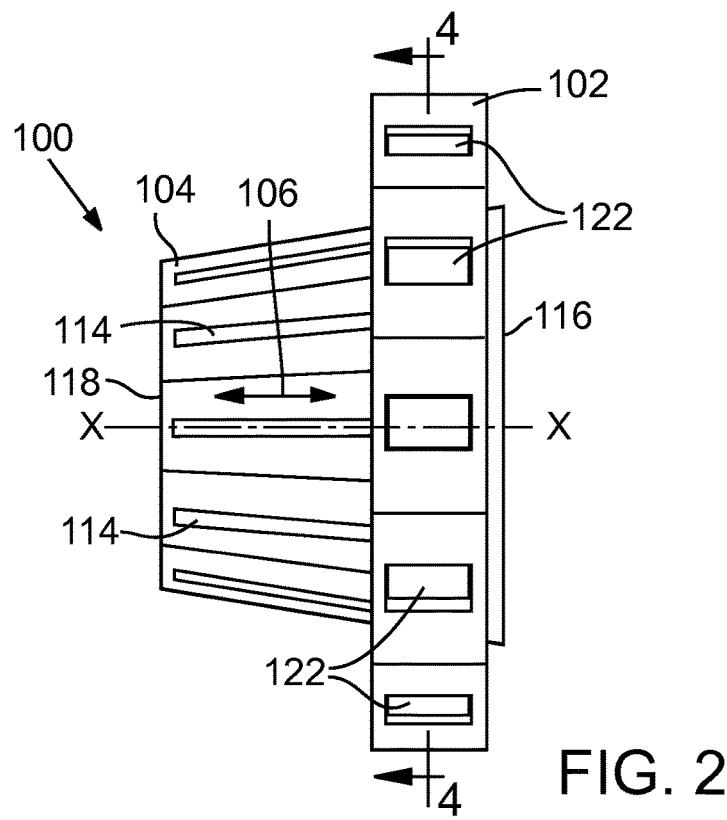
FIG. 2 shows a side elevation view of the crimper of FIG. 1 in a first position, corresponding to an open configuration.
Figure 3:
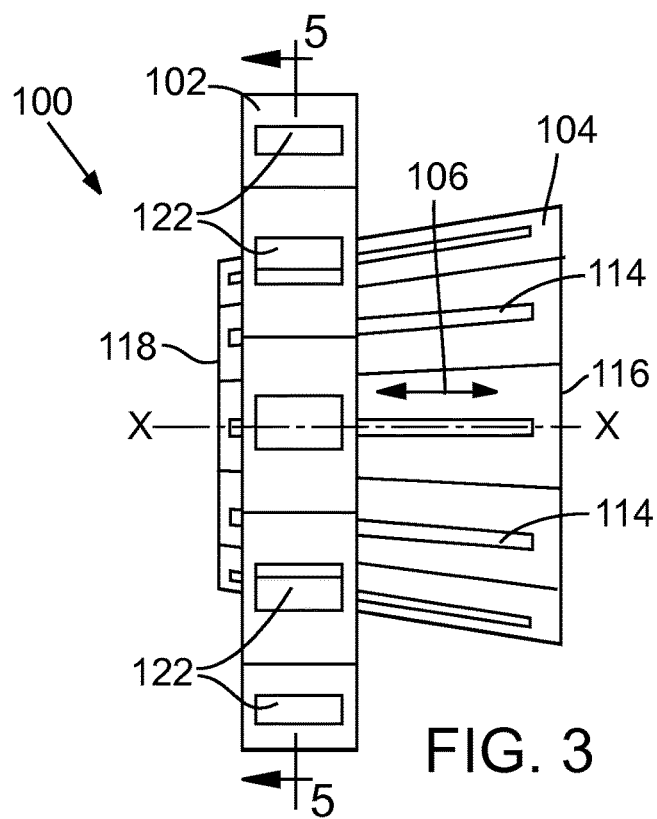
FIG. 3 shows a side elevation view of the crimper of FIG. 1 in a second position, corresponding to a closed configuration.
Figure 4:
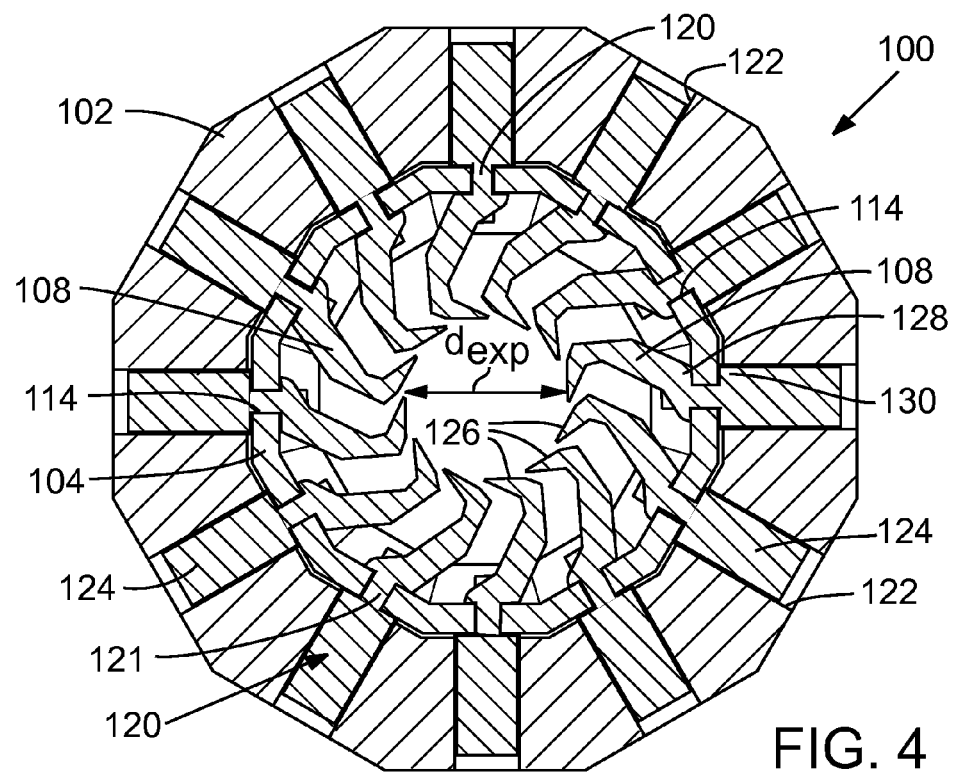
FIG. 4 shows a cross-section view of the crimper of FIG. 2, taken along section line 4-4 in FIG. 2.
Figure 5:
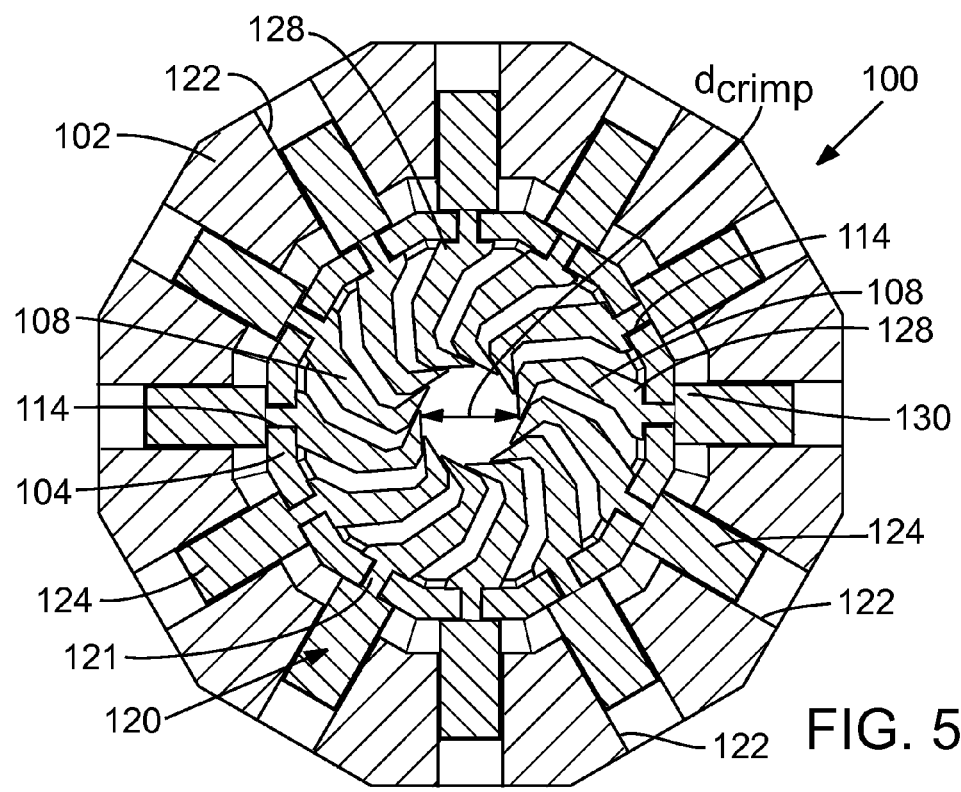
FIG. 5 shows a cross-section view of the crimper of FIG. 3, taken along section line 5-5 in FIG. 3.
Figure 6:
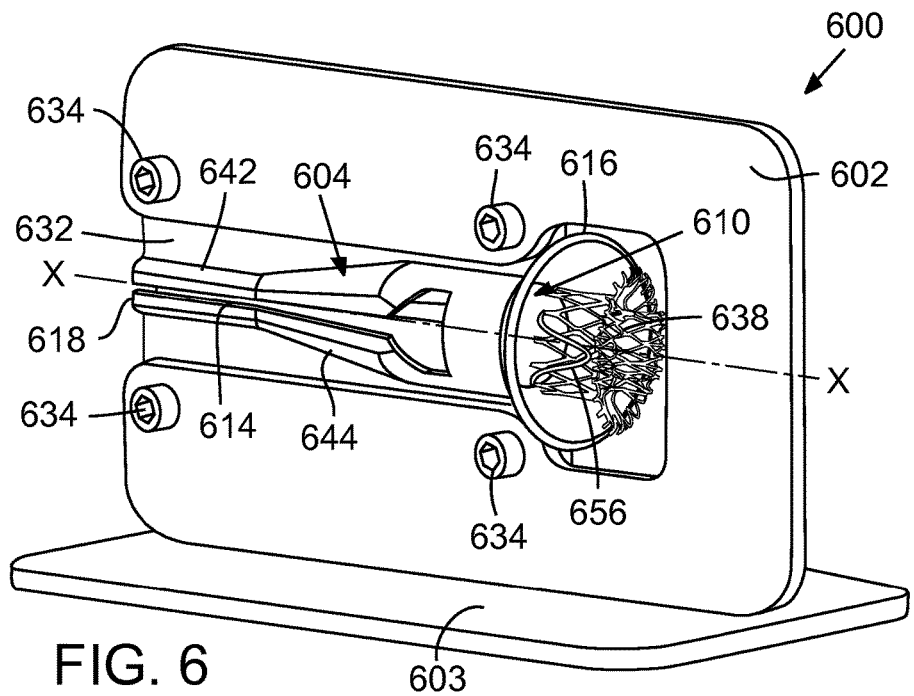
FIG. 6 shows a perspective view of the back of another embodiment of a crimping device mounted on a stand and base according to the present disclosure.

As best seen in FIGS. 1-3, the crimping device 100 can include an outer frame, such as a stand, 102 and an inner frame, or driver, such as a cone, 104. The outer frame 102 can be configured to support the cone 104 and a plurality of crimping jaws 108 (FIGS. 4-5). The cone 104 can be configured to move with respect to the outer frame 102 in the directions indicated by double-headed arrow 106 (e.g., back and forth along the longitudinal central axis X of the cone 104). Such motion of the cone 104 can cause radial crimping of a medical device positioned within the portions of the crimping jaws 108 that extend into the interior of the cone 104 (FIGS. 4-5) and that are arranged about the axis X in a plane perpendicular to the X axis. Thus, the crimping jaws 108 are driven by a mechanism having motion out of a plane of crimping; in this example, movement of the cone 104 is perpendicular to a crimping plane and the direction of the radial crimping force applied by jaws 108 to the medical device.

The crimping jaws 108 define a variable-sized iris or aperture between their inner ends 126. The variable-sized aperture can vary between a larger diameter ($d_{exp}$) that can accommodate a stented prosthetic valve in an original, expanded configuration and a smaller diameter ($d_{crimp}$) that corresponds with the desired crimped delivery diameter of the stented prosthetic valve. The inner portion of the crimping jaws 108 can be surrounded by the outer frame 102 such that the outer frame defines a generally cylindrical cavity therewithin that constrains the crimping jaws 108.

Still with reference with FIGS. 1-3, the outer frame 102 can be, for example, a 12-sided polygon shaped stationary stand. In other embodiments, outer frame 102 can be substantially circular or can have other suitable shapes as well. The outer frame 102 can be annular, such that it has a central hole or opening 110 through which the cone 104 can move. As shown in FIG. 1, the central opening 110 of the outer frame 102 can have a "diameter" or greatest dimension of $d_{in}$. The dimension $d_{in}$ can be at least as great as the maximum outer diameter $d_{max}$ of the cone 104 such that the opening 110 of the outer frame 102 is large enough such that the cone 104 can slide back and forth through the outer frame 102. When positioned as shown in FIG. 1, there may be a substantial gap between the external surface 112 of the cone 104 and the outer frame 102, due to the difference between the minimum diameter $d_{min}$ of the cone 104 and the maximum diameter $d_{max}$ of the cone 104.

The cone 104 can comprise a frustoconical annular body and a plurality (e.g., equal to the number of jaws) of jaw guides, such as slots 114, extending from near a first cone end portion 116 adjacent $d_{max}$ to near a second cone end portion 118 adjacent $d_{min}$. As shown in FIGS. 4-5, the slots 114 can essentially guide the cone 104 as it moves through the outer frame 102, due to extension portions 120 of the crimping jaws 108 that extend from inner portions 128 of the jaws 108 through the slots 114 and into corresponding receiving holes, or jaw support holes, 122 formed in the outer frame 102. As best seen in FIGS. 4-5, the extension portions 120 of each crimping jaw 108 can comprise an engagement portion 121 that extends through a corresponding slot 114 in the cone 104 and an outer portion 124 that aligns with a corresponding receiving hole 122 in the outer frame 102. The outer portion 124 of the jaw 108 can comprise an enlarged portion disposed within a corresponding receiving hole 122 in the outer frame 102.

As the cone 104 is moved axially with respect to the outer frame 102, the engagement portion 121 of each of the crimping jaw extensions 120 slides within its respective cone slot 114. The design of the crimping jaws 108 (e.g., with a narrow engagement portion 121, a widened inner portion 128 positioned adjacent the interior of the cone 104, and a widened outer portion 124 positioned adjacent the exterior of the cone 104 and inside the receiving holes 122 of the outer frame 102) forces the crimping jaws' inner ends 126 to move closer together as the jaw extensions 120 slide through the cone slots, thus reducing the variable-sized aperture formed by the inner ends 126 of the crimping jaws.

In this manner, movement of the cone 104 from an original configuration (FIG. 4) to a crimping configuration (FIG. 5) can cause the crimping jaws 108 to move from an original configuration accommodating a medical device having an expanded diameter $d_{exp}$ (FIG. 4) to a crimping configuration that crimps the medical device to a crimped diameter $d_{crimp}$ (FIG. 5). In some embodiments, the crimping device 100 can be used to crimp a medical device directly onto a delivery system. For example, crimping device 100 can crimp a balloon-expandable stent or stented prosthetic valve (e.g., a prosthetic heart valve comprising a balloon-expandable metal stent and tissue leaflets supported by the stent) directly onto an inflatable balloon mounted on a delivery catheter. In other embodiments, the crimping device 100 can crimp a self-expandable medical device directly onto a delivery system. In some embodiments, the crimping device 100 can crimp a self-expandable medical device, which can then be moved directly into a transfer system in its crimped configuration, as described below, for transport to a different location.

The cone 104 can be moved manually (e.g., by hand) in some embodiments. In other embodiments, movement of the cone 104 can be controlled by an automated or computer-controlled mechanism. Also, radial movement of the jaws 108 can be accomplished by holding the cone 104 stationary and moving the outer frame 102 relative to the cone. For example, while the embodiment shown in FIGS. 1-5 has been described such that the cone 104 is moved with respect to the outer frame 102, the opposite is also possible. In other words, in some embodiments, the outer frame 102 can be moved with respect the cone 104. While the outer frame 102 is not shown with any additional structure or hardware, the outer frame 102 can include additional parts or portions that would better configure the outer frame to be placed securely on a surface, such as a table. In some embodiments, the outer frame 102 can comprise a stand that include a base that supports the annular outer frame 102, and/or a clamp or other device that secures the stand to the table or work surface, in order to substantially prevent movement of the outer frame 102.

In other embodiments, out-of-plane surfaces other than the outer and/or inner surfaces of a conical inner frame can be utilized to drive the crimping jaws closer together. For example, the crimping device 200 shown in FIGS. 22-25 includes an inner frame, or driver, 203 that comprises a plurality of sloped or inclined guiderails 204 that can drive the motion of the crimping jaws 208 via bearings 230 (FIG. 25) at the engagement portion of the jaws. The sloped guiderails 204 can be arranged to form a conical or frusto-conical shape, with a guiderail 204 provided for each of the crimping jaws 208. The guiderails 204 can be rigidly secured at their opposing ends to a first end portion 216 and a second end portion 218. A bearing 230 positioned within each crimping jaw 208 can allow for smooth motion of the guiderails 204 through the crimping jaws 208. As the crimping jaws 208 are moved along the sloped guiderails 204 (e.g., as the inner frame 203 and the outer frame 202 move axially relative to each other), the jaws 208 move radially closer together, thereby being configured to crimp a medical device in the radial direction (e.g., out of plane with the motion of the inner frame 203) within a variable-sized iris or aperture 226.

Figure 22:
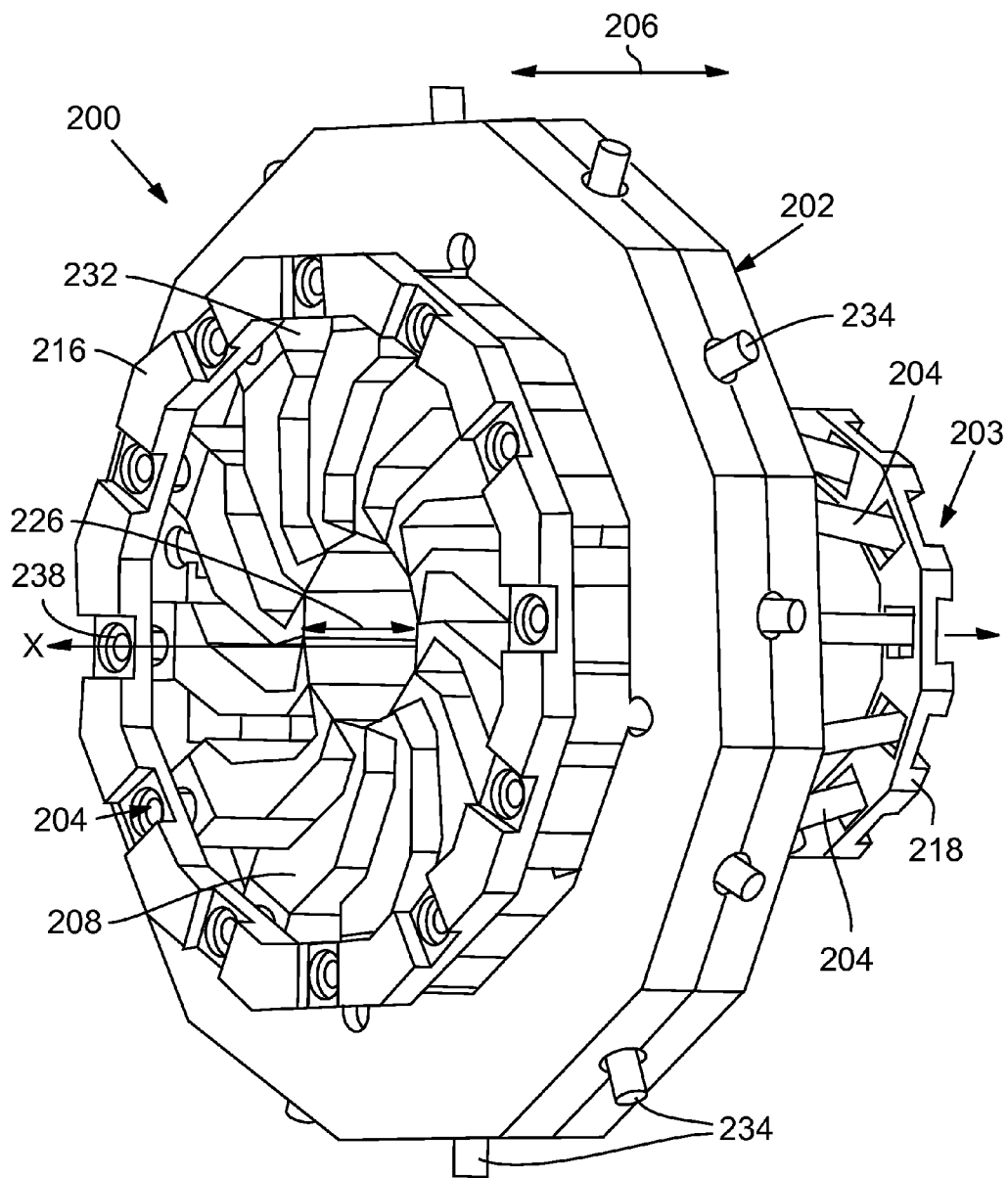
FIG. 22 is a perspective view of another embodiment of a crimping device.
Figure 23:
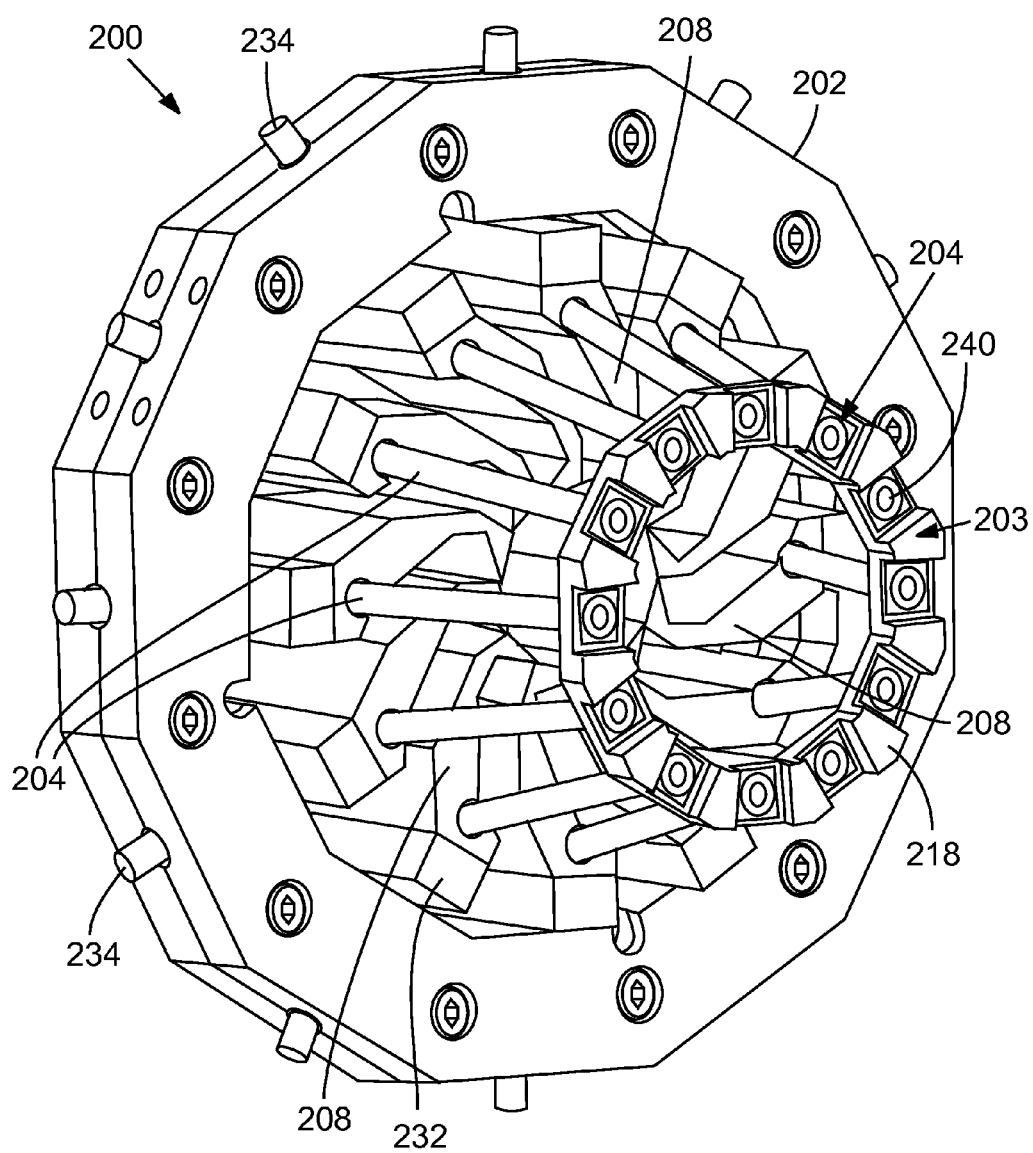
FIG. 23 is another perspective view of the crimping device of FIG. 22.

The crimping device 200 can include an outer frame 202, an inner frame 203 comprising a plurality of guiderails 204 arranged in a generally conical or frustoconical shape, and a plurality of crimping jaws 208. The outer frame 202 can be configured to surround and/or support the inner frame 203 and crimping jaws 208. The outer frame 202 can be configured to move relative to the inner frame 203 in the directions indicated by double-headed arrow 206 (e.g., back and forth along the guiderails 204). Such relative motion between the outer frame 202 and the inner frame 203 can cause radial crimping of a medical device positioned within the crimping jaws 208 that extend into the conical interior of the inner frame 203 and that are arranged about the axis X (FIG. 22). Thus, the crimping jaws 208 are driven by a mechanism having motion out of a plane of crimping; in this example, relative movement between the outer frame 202 and the inner frame 203 is perpendicular to a crimping plane and the direction of the radial crimping force applied by jaws 208 to the medical device. In some embodiments, the end portions 216, 218 and guiderails 204 of the inner frame 203 can be configured to move together as a unit with respect to a stationary outer frame 202, acting as a driver, in order to actuate the crimping motion of the jaws 208, and in other embodiments, the outer frame 202 and jaws 208 can be configured to move together as a unit with respect to a stationary inner frame 203 in order to actuate the crimping motion of the jaws 208.

The outer frame 202 can be, for example, a 12-sided polygon shaped annular frame. In other embodiments, outer frame 202 can be substantially circular or can have other suitable shapes as well. The outer frame 202 can be annular, such that it has a central hole or opening within which the inner frame 203 and crimping jaws 208 can move.

The guiderails 204 can extend from the first end portion 216 of the inner frame 203 corresponding to a maximum expanded aperture diameter to the second end portion 218 of the inner frame corresponding to a minimal crimped aperture diameter. When the outer frame 202 is positioned nearest the first end portion 216, the crimping jaws 208 are farthest apart and the variable-sized iris 226 is at an expanded, maximum diameter. When the outer frame 202 is positioned nearest the second end portion 218, the crimping jaws 208 are closest together and the variable-sized iris 226 is at a crimped, minimal diameter.

The crimping jaws 208 each can be provided with an end plate 232 positioned adjacent the outer frame 202 and mounted to the crimping jaw 208 adjacent the guiderails. The guiderails 204 can extend at an angle through both the crimping jaws 208 and the end plates 232 (best seen in FIG. 24). A bearing 230 (seen in FIG. 25 where one end plate 232 has been removed to show the underlying structure) can be positioned such that it extends at least partially through each respective end plate 232 and crimping jaw 208, thereby providing a smooth surface through which each respective guiderail 204 can slide. Each respective end plate 232 can be secured to the end of a respective jaw 208 (e.g., with screws) such that a respective bearing 230 is held between or within the end plate 232 and the jaw 208.

A first end 238 of each guiderail 204 can be fixedly coupled to the first end portion 216, such as by a screw or other fastener, friction, welding, and/or adhesion (not shown). Similarly, a second end 240 of each guiderail 204 can be coupled to the second end portion 218, such as by a screw or other fastener, welding, friction, and/or adhesion. Thus, the guiderails 204 can be configured so as to be essentially immobile with respect to the first and second end portions 216, 218. In this manner, the guiderails 204 and end portions 216, 218 collectively form a rigid inner frame 203 that is configured to move the jaws 208 closer together and farther apart from each other upon relative longitudinal axial movement between the inner frame 203 and the jaws 208.

Figure 24:
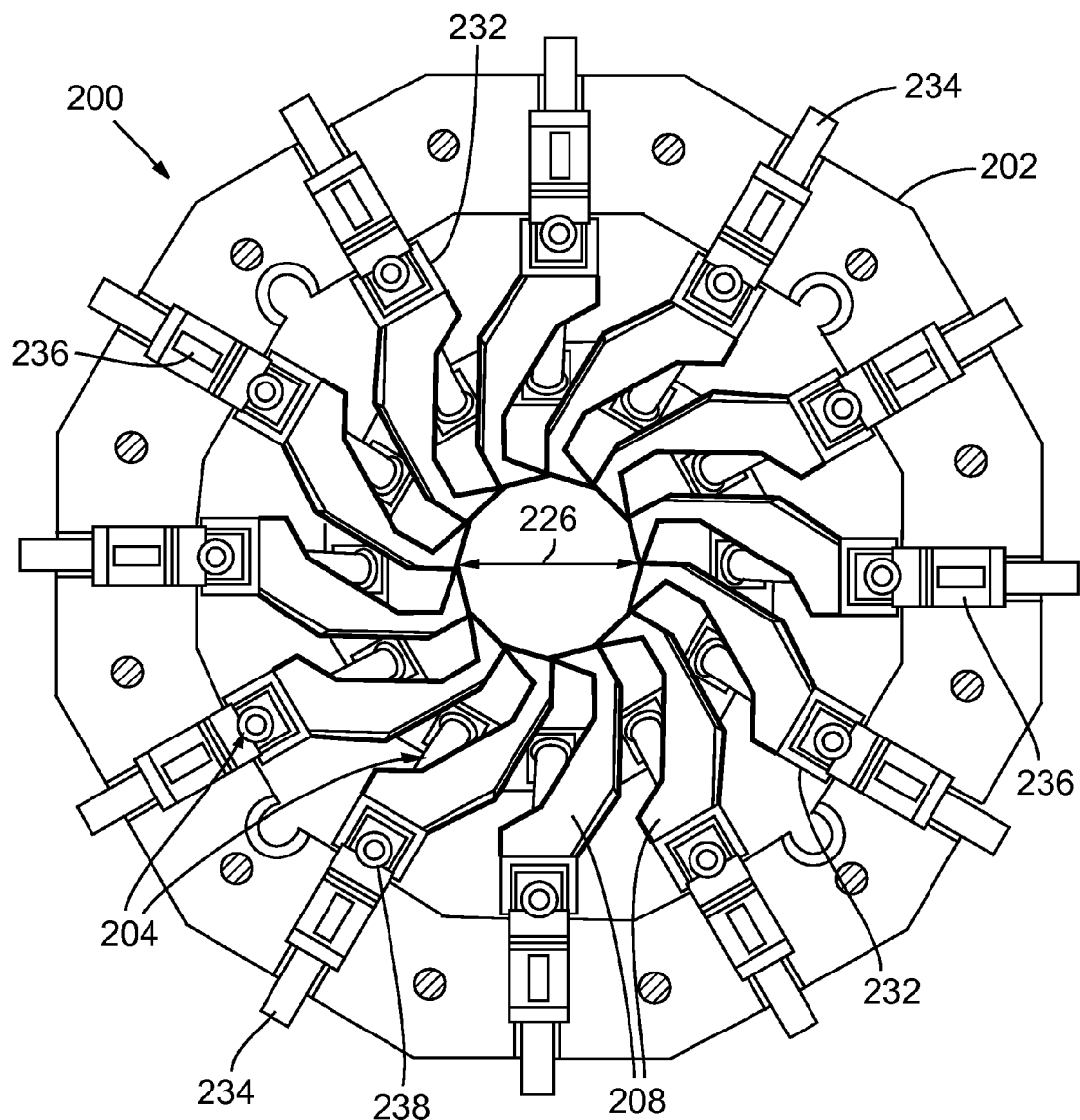
FIG. 24 is a front elevation view of the crimping device of FIG. 22, with part of an outer frame removed to show additional structure.
Figure 25:
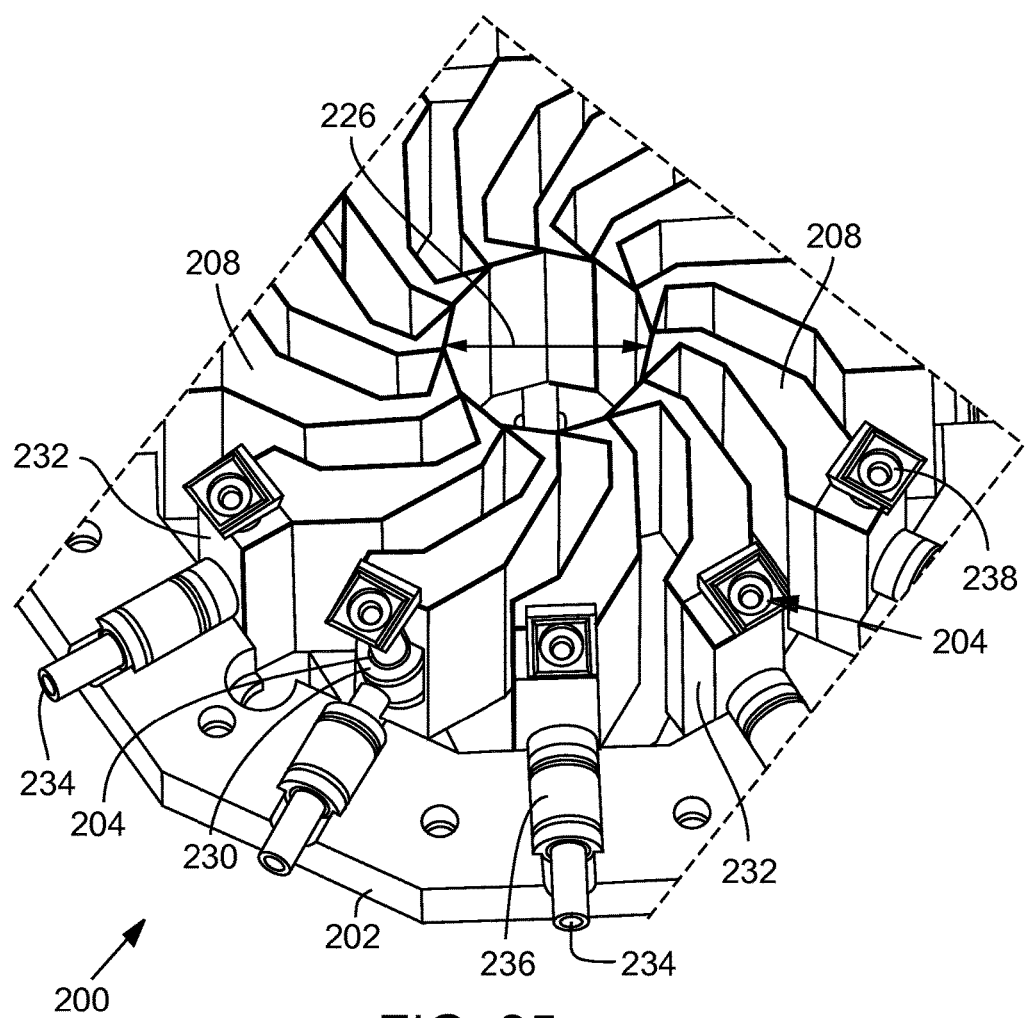
FIG. 25 is a partial perspective view of the crimping device of FIG. 22, with one of the jaw tops removed.
Figure 26:
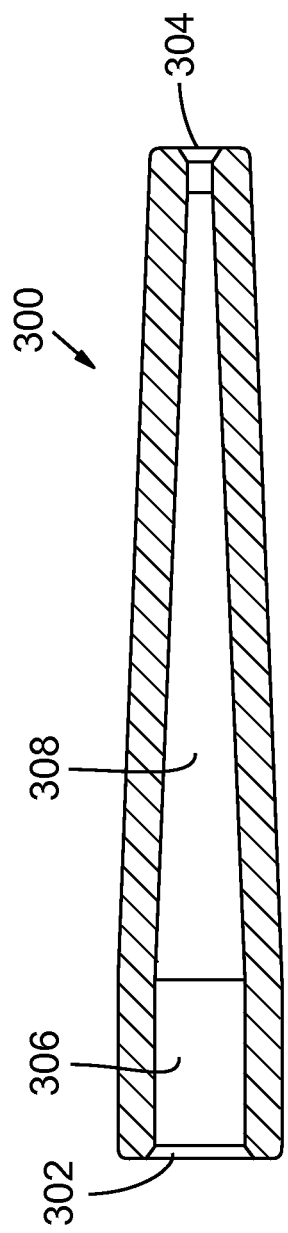
FIG. 26 is a cross-sectional side view of an exemplary embodiment of a funnel-shaped crimping device.
Figure 27:
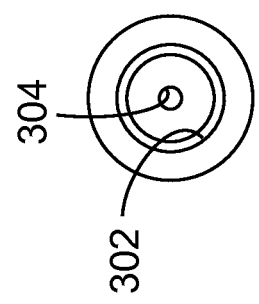
FIG. 27 is an end view of the crimping device of FIG. 26.

As the inner frame 203 is moved axially relative to the outer frame 202, each of the guiderails 204 slides through its respective bearing 230 in a corresponding crimping jaw 208 and end plate 232. The crimping device 200 can additionally include a plurality of radial guiderails 234, such as outer portions of the jaws, positioned radially perpendicular to the longitudinal axis X. FIGS. 24-25 show the crimping device 200 with the first end portion 216 removed and the outer frame 202 partially cut-away in order to better show the radial guiderails 234 and their respective radial bearings 236, which are secured within radial openings in the outer frame 202 to provide a smooth surface for radial movement of the radial guiderails 234 through the outer frame 202. In some embodiments, the inner end of each radial guiderail 234 can be secured to a respective end plate 232 to prevent longitudinal or angular movement of the jaws 208 relative to the outer frame 202 and constrain the motion of the crimping jaws 208 in the plane of crimping (e.g., in the radial direction). The crimping jaws 208 are therefore forced to move radially closer together (reducing the size of the iris 226) as the guiderails 204 slide through the crimping jaws 208 in a direction along the longitudinal axis X, causing the outer frame 202 and the second end portion 218 to be moved closer together (FIG. 22). Conversely, as the guiderails 204 are moved in the opposite direction, causing the outer frame 202 and first end portion 216 to be moved closer together, the crimping jaws 208 are forced to move farther apart (enlarging the size of iris 226). One or both of the outer frame 202 and the inner frame 203 can be moved manually (e.g., by hand) in some embodiments. In other embodiments, relative movement between the inner frame 203 and the outer frame can be provided by an electric motor, hydraulics, pneumatics, or equivalent devices. In some embodiments, movement can be controlled by an automated or computer-controlled mechanism.

As compared with the prior art crimping devices, disclosed crimper embodiments can provide several advantages. For example, the sloped guiderails or conical surface (or other sloped surface) can be designed to create a particular mechanical advantage. Because the slope of the guiderails or cone (e.g., the out-of-plane surface) determines the mechanical advantage of the crimping device, the guiderails or cone can be designed with a steeper slope to decrease the mechanical advantage (e.g., require more force to perform the crimping), or it can be designed with a gentler or shallower slope to increase the mechanical advantage (e.g., reduce the amount of force required to perform the crimping).

The degree of sloping can also be used to control the precision of the crimping device in disclosed embodiments. For example, a steeper guiderail or cone slope will require less travel out of the crimping plane (e.g., less travel along the longitudinal axis of the cone) to compress the crimping radius a given amount, thereby reducing the amount of precision. On the other hand, reducing the slope of the guiderail or cone can allow for greater travel of the guiderails or cone with respect to the outer frame, and thus greater precision in crimping.

Disclosed embodiments of a crimping device can also increase the portability of such crimping devices, in that they allow for smaller crimping devices for a particular device than prior art crimping devices would. For example, for larger medical devices, such as prosthetic valves having an expanded diameter of more than about 29 mm, prior art crimping devices sized to crimp such valves typically are heavy and large, and thus not easily portable because the in-plane mechanisms require an in-plane size increase to accommodate larger medical devices. In prior art crimpers, both the diameter of the crimper and the size of the handle (to increase the mechanical advantage) had to increase as the diameter of the medical device was increased. By contrast, currently disclosed embodiments allow for the increased diameter of the prosthetic device to be accommodated both in the length of the guiderails or cone (out of the crimping plane) and in the diameter of the crimper, thus leading to less overall size increases and increased portability.

Additionally, while typical prior art crimping devices restrict or severely limit access to the crimping jaws, currently disclosed embodiments can allow for maximum access to the crimping jaws if necessary. This can advantageously allow currently disclosed crimping devices to be used with valves or other medical devices having portions that are not crimped, or portions that are moved to a delivery state after a main body of the medical device is radially crimped. For example, a prosthetic mitral valve can include anchors connected to a generally tubular main body. The access to the fronts and backs of the crimping jaws provided by the presently disclosed crimping devices can allow for correct positioning of the main body of the valve within the crimping device such that the anchors (or other appendages) are not crimped with the main body.

FIGS. 6 to 9 show another embodiment of a crimping device according to the present disclosure. Crimping device 600 generally consists of a stand 602 supported on a base 603, and a split funnel 604. The split funnel 604 can crimp a medical device, such as stent frame 638, as the stent frame 638 is moved through the central opening 610 of the split funnel 604, from a first, larger funnel end 616 towards a second, smaller funnel end 618. The stent frame 638 can be moved (e.g., pushed, pulled, or otherwise guided) all the way through the split funnel 604 (e.g., the stent frame 638 can exit the split funnel 604 at the second end 618, which corresponds to the smallest diameter of the split funnel 604, and therefore also to the crimped diameter of the medical device crimped via the crimping device 600). In some embodiments, the stent frame 638 can be the frame of a prosthetic heart valve.

In some embodiments, a portion of the medical device being crimped in the crimping device 600 can extend through one or more slots 614 formed in the split funnel 604. For example, the split funnel 604 can essentially be a funnel that has been split along a portion of its length, to form an upper half 642 and a lower half 644, separated by one or more slots 614. In the example shown in FIGS. 6-9, the split funnel 604 has two slots 614, one on either side of the split funnel 614, but more or fewer slots 614 are also possible. As shown, the slots 614 can extend only along a portion of the length of the split funnel 604. For example, the slots 614 in FIGS. 6-9 extend from the second funnel end 618 towards the first funnel end 616, but the slots stop before reaching the first funnel end 616. Thus, a portion of the split funnel 604 can be whole (e.g., not split) in some embodiments.

Figure 7:
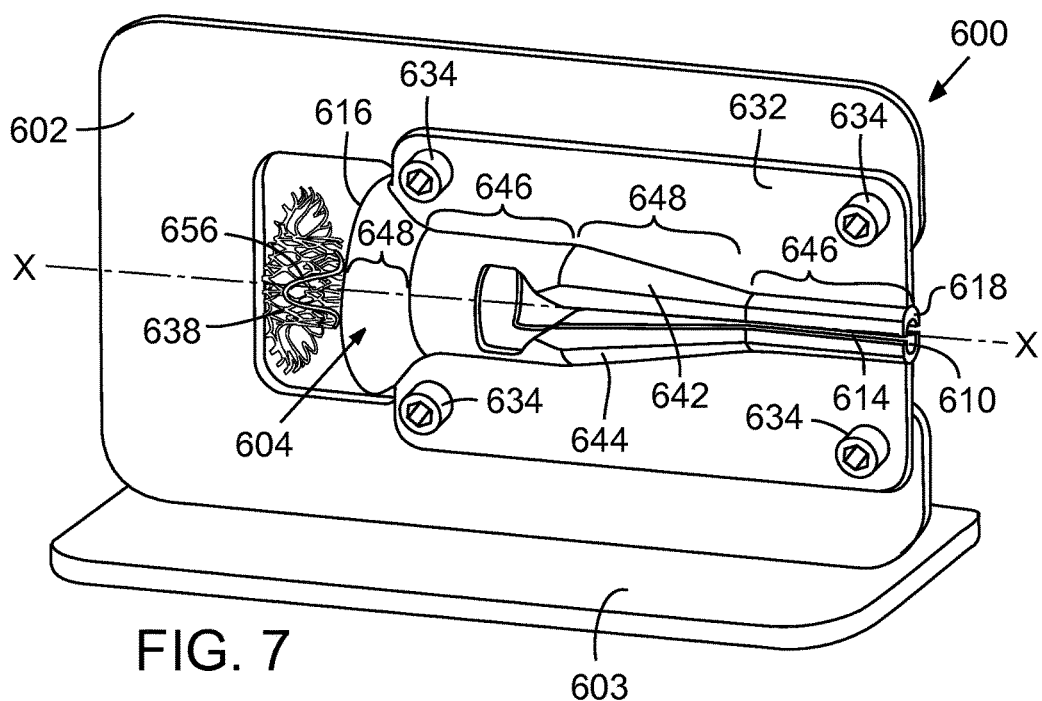
FIG. 7 shows a perspective view of the front of the crimping device of FIG. 6.
Figure 8:
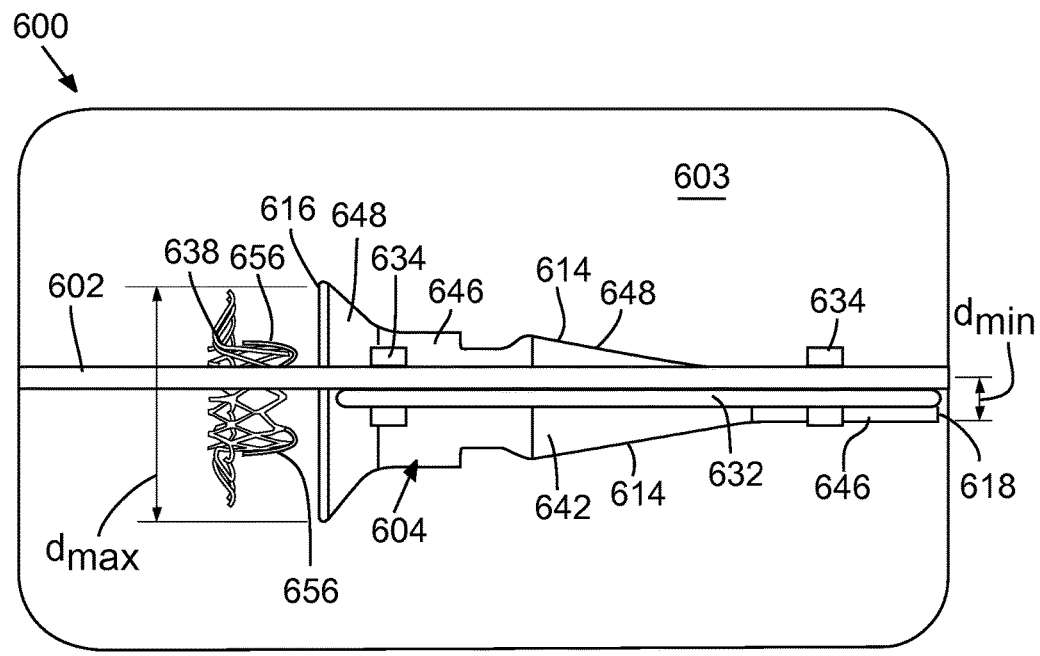
FIG. 8 shows a top view of the crimping device of FIG. 6.
Figure 9:
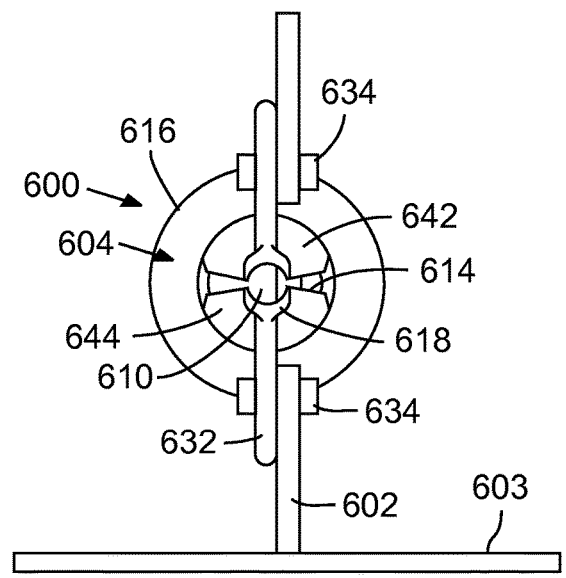
FIG. 9 shows an elevation view of the crimping device of FIG. 6.
Figure 15:
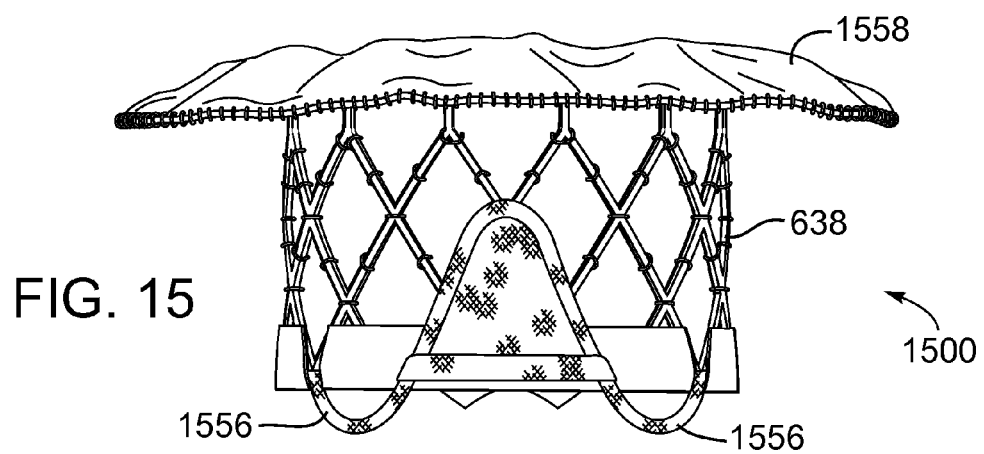
FIG. 15 shows a side elevation view of one embodiment of a stented prosthetic valve.
Figure 16:
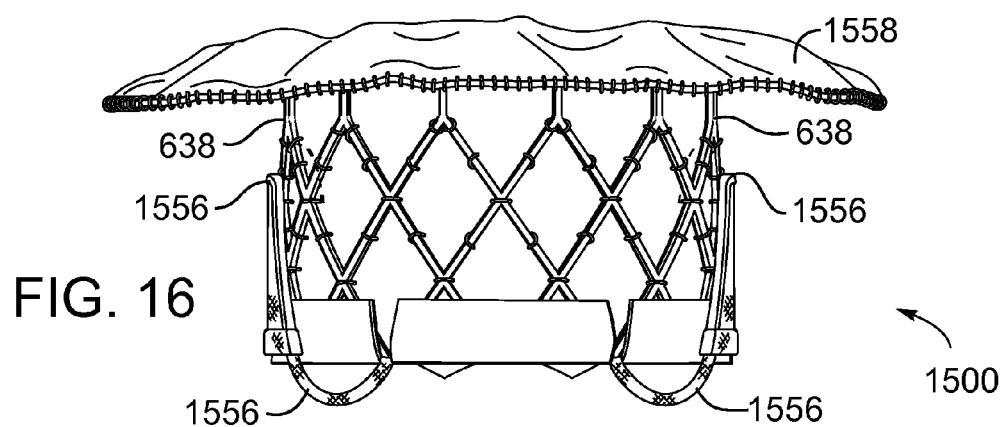
FIG. 16 shows the stent prosthetic valve of FIG. 15, rotated ninety degrees about the longitudinal axis.

The central opening 610 of the split funnel 604 decreases in diameter along its longitudinal axis X, decreasing from a maximum diameter $d_{max}$ adjacent the first funnel end 616 to a minimum diameter $d_{min}$ adjacent the second funnel end 618 (FIG. 8). The diameter can decrease continuously along the length of the split funnel 604 in some embodiments. In some embodiments, the diameter can change (decrease) at different rates at different segments along the length of the split funnel 604. As shown in FIGS. 7-8, in some embodiments, the split funnel 604 can include one or more portions 646 having a substantially constant diameter, and one or more portions 648 having a decreasing diameter.

Figure 19:
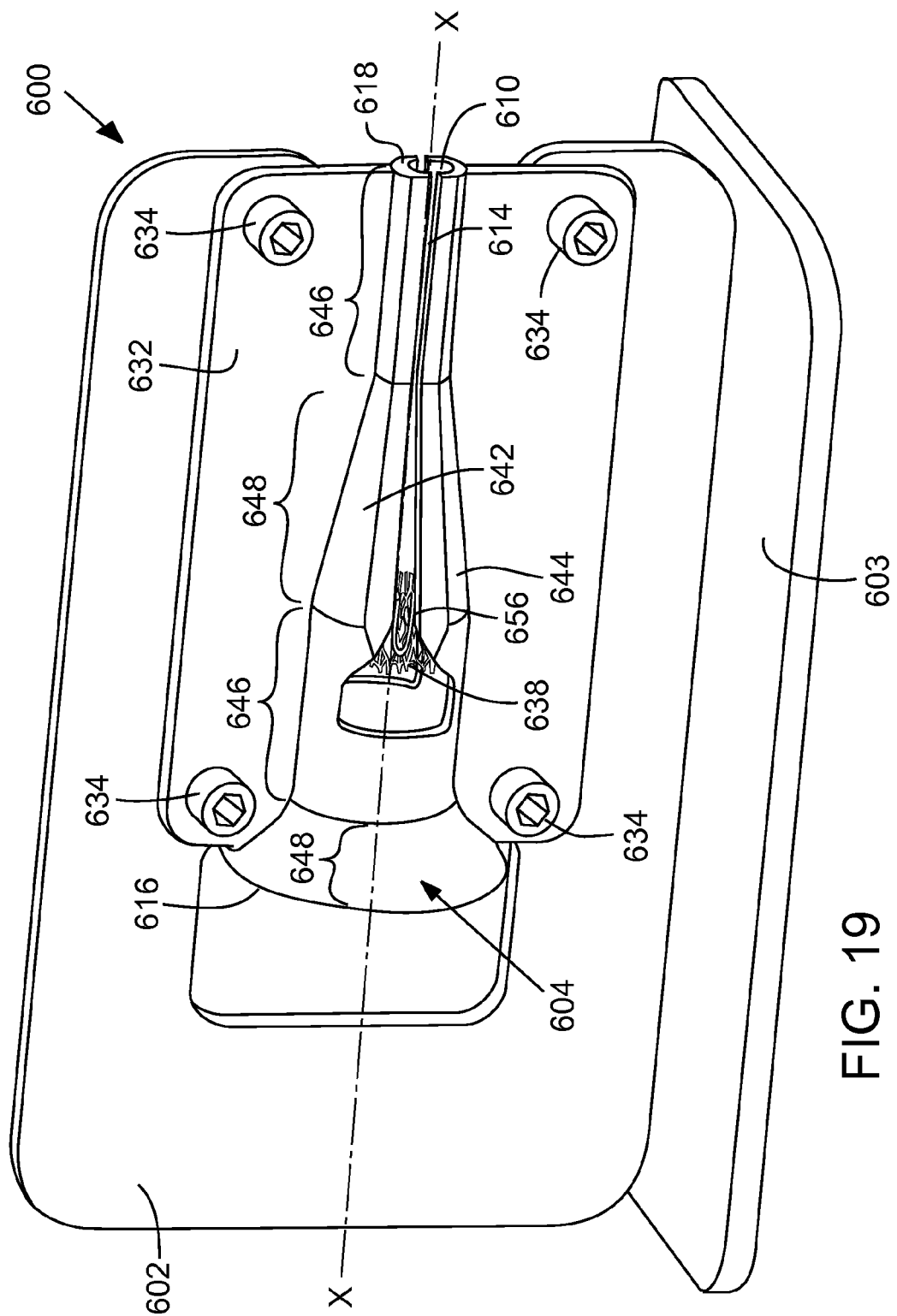
FIG. 19 shows the stented prosthetic valve of FIGS. 15-16 being crimped in the crimping device of FIGS. 6-9.

In some instances, the medical device to be crimped by crimping device 600 may include portions that are crimped and portions that remain in an expanded configuration. For these types of medical devices, conventional crimping devices cannot be used because they are designed to crimp the entire medical device, and do not allow for portions to remain uncrimped (e.g., expanded). Advantageously, the slots 614 of the crimping device 600 can allow for portions of a medical device to remain in an expanded configuration, while the rest of the device is crimped. For example, as stent frame 638 is crimped and moved through the split funnel 614, a portion of the stent frame 638 can extend through one or more of the slots 614, and thus not be crimped because those portions extending through the slots 614 are not inside the central opening 610 of the split funnel 604, and thus are substantially unaffected by the decreasing diameter of the split funnel 604. In one embodiment, as shown in FIG. 19, the stent frame 638 can include one or more anchors 656, where the anchors are positioned to extend through the funnel slots 614 as the stent frame 638 is moved through the split funnel 604. In this manner, the main body of the stent frame 638 can be crimped in the crimping device 600, while the anchors 656 are not directly crimped by the crimping device 600.

FIG. 13 shows an embodiment of the stent frame 638, with one or more sutures 640 coupled to the stent frame 638. Sutures 640 can be used to facilitate crimping of the stent frame 638. For example, as shown, the sutures 640 can be quite long, such as several times longer than the stent frame 638 itself. The sutures 640 can be positioned such that they pass through the central opening 610 of the split funnel 604, extending out of the second funnel end 618, opposite the first funnel 616 where the stent frame 638 enters the split funnel 604. The sutures 640 can be long enough such that there is enough length extending out of the second funnel end 618 to grasp and pull, thereby pulling the stent frame 638 through the split funnel 604. The sutures 640 can be removed once the stent frame 638 has been moved through the crimping device. In some embodiments, such as for self-expanding prosthetic valves, the crimped medical device can be pulled through the crimping device 600 and moved directly onto a delivery device or into a delivery sheath. In some embodiments, a self-expanding prosthetic valve can be pulled through the crimping device 600 and moved directly into a transfer system as described below.

Figures 17, 18:
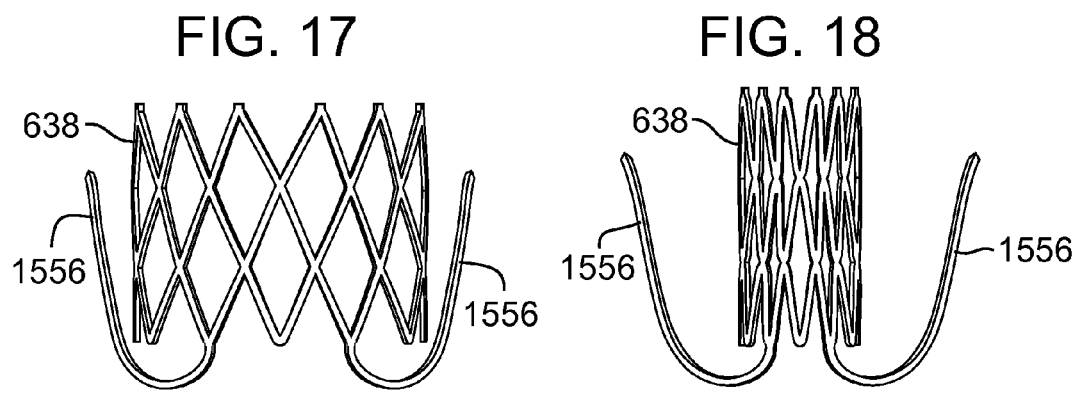
FIG. 17 shows a side elevation view of one embodiment of a stent frame for use with a prosthetic valve, in an expanded configuration.
FIG. 18 shows the stent frame of FIG. 17 in a radially compressed configuration.

The stent frame 638 can be a stent frame for use with a self-expandable stented prosthetic valve, such as the stent prosthetic valve disclosed in U.S. patent application Ser. No. 12/959,292 (hereafter "the '292 application), which is disclosed herein by reference. FIGS. 15-18, further described in the '292 application, show one embodiment of a stented prosthetic valve 1500 having anchors 1556, an atrial sealing member 1558, and stent frame 638. In particular embodiments, the valve 1500 is a prosthetic mitral valve that can be deployed in the native mitral annulus. The sealing member 1558 can be deployed in the left atrium and the anchors 1556 can be deployed in the left ventricle behind the native mitral valve leaflets. The anchors 1556 can extend through the slots 614 of the split funnel 604 as the prosthetic valve 1500 is moved through the crimping device 600, as shown in FIG. 19. In this manner, the main body of the prosthetic valve 1500 (e.g., the stent frame 638 and the atrial sealing member 1558) can be crimped in the crimping device 600, while the anchors 1556 remain uncrimped. FIGS. 17-18 show one embodiment of a stent frame 638 having anchors 1556 before crimping (FIG. 17) and after crimping (FIG. 18) by presently disclosed crimping devices. As seen in FIGS. 17-18, the crimping device can crimp the main body of the stent frame 638, while the anchors 1556 remain in an expanded configuration.

In some embodiments, the anchors 1556 can be compressed separately, after the main body is radially compressed by the crimping device 600 and loaded into a delivery sheath. An outer delivery sheath can then be slid over the anchors 1556 to retain them in a compressed position. This allows the stented prosthetic valve 1500 disclosed in the '292 application to be deployed in two stages: first the anchors are deployed as the outer delivery sheath is removed, and second the main body is deployed as the inner delivery sheath is removed.

Returning to FIGS. 6-9, the split funnel 604 can be coupled to a funnel plate 632 (e.g., formed integral with, welded, adhered, fused, or otherwise coupled to) that facilitates coupling to a stand 602 and base 603. The base 603 can, for example, be positioned and/or secured (e.g., clamped) onto a work surface such as a table or other flat surface. The base 603 can be configured to support the stand 602 and split funnel 604 as a medical device is crimped in the crimping device 600. In some embodiments, as shown in FIGS. 10 and 11, the funnel plate 632 and the stand 602 can each be provided with one or more fastening holes 636. In the embodiment shown, the funnel plate 632 and the stand 602 each have four fastening holes 636. Each fastening hole 636 on the funnel plate 632 can be positioned to align with a respective fastening hole 636 on the stand 602, in order to secure the split funnel 604 to the stand 602 and base 603 for operation. Returning to FIGS. 6-9, one or more fasteners (e.g., screws 634) can be used to couple the funnel plate 632 to the stand 602.

During use, a medical device that has been crimped often must be transported at least a short distance to a different location, where it will be loaded onto a delivery system and implanted into a patient. Depending on the characteristics of the particular medical device being crimped, in some instances, the medical device may tend to disadvantageously expand again once removed from the crimping device. In order to prevent such re-expansion after crimping, a transfer system can be used to transport the crimped medical device after crimping. FIG. 12 shows a schematic, simplified view of one embodiment of a transfer system 1200 that can be used to transport a crimped medical device and prevent re-expansion. The transfer system 1200 generally can include a support structure 1202 and a restraint 1204. The restraint 1204 can be a generally tubular restraint and can include one or more slots 1214 separating an upper restraint half 1242 from a lower restraint half 1244. The support structure 1202 can be configured to position the upper restraint half 1242 with respect to the lower restraint half 1244. The support structure 1202 can additionally provide a surface which can be held during transport.

The transfer system 1200 can be configured to resist any force exerted on it by a crimped medical device tending to re-expand, so as to prevent such re-expansion of the medical device. In some embodiments, a portion of the crimped medical device can extend through the slots 1214. For example, in embodiments where not all portions of a device are crimped, the non-crimped portions of the medical device can extend through the slots 1214 as the otherwise crimped device is being transported. In one embodiment, the restraint 1204 can include two slots 1214, spaced about 180 degrees apart from one another, and can be configured to allow the anchors 1556 of prosthetic valve 1500 (FIGS. 15-16) to extend through the slots, while the restraint 1204 retains the crimped configuration of the main body of the prosthetic valve.

FIG. 14 shows a schematic representation of the transfer system 1200 of FIG. 12 in a position to transfer a crimped medical device into a delivery sheath 1454 of a delivery device. A tool, such as a pushing tool 1450, can be moved in the direction of arrow 1452 such that it at least partially enters the tubular restraint 1204, thereby displacing the crimped medical device being held within the tubular restraint 1204. A delivery sheath 1454 can be positioned adjacent the transfer system 1200, opposite the pushing tool 1450. Thus, as the pushing tool 1450 pushes the crimped medical device through the tubular restraint 1204 of the transfer system 1200, the crimped medical device can be pushed directly into the delivery sheath 1454. In one specific embodiment, the delivery sheath 1454 can include one or more slots 1414. For example, the delivery sheath 1454 can include two slots 1414, spaced about 180 degrees apart, to accommodate the anchors 1556 of prosthetic valve 1500 (FIGS. 15-16) which are left uncrimped by the crimping device 600. An outer delivery sheath can then be placed onto the delivery sheath 1454, thereby compressing the anchors 1556 for delivery.

FIGS. 20-21 illustrate one embodiment of a delivery system 2000 for implanting a stented prosthetic valve (e.g., valve 1500) that is crimped by the disclosed crimping devices. The delivery system 2000 can comprise a series of concentric shafts and sheaths aligned about a central axis and slidable relative to one another in the axial directions. The delivery system 2000 can comprise a proximal handle portion 2002 for physician manipulation outside of the body while a distal end portion, or insertion portion, 2004 is inserted into the body.

The delivery system 2000 can comprise an inner shaft 2006 that runs the length of the delivery system and comprises a lumen through which a guidewire (not shown) can pass. The inner shaft 2006 can be positioned within a lumen of a pusher shaft 2010 and can have a length that extends proximally beyond the proximal end of the pusher shaft and distally beyond the distal end of the pusher shaft The delivery system 2000 further comprises an inner sheath 2014 positioned concentrically around at least a distal portion of the pusher shaft 2010. The inner sheath 2014 is axially slidable relative to the pusher shaft 2010 between a delivery position and a retracted position. In the delivery position, a distal end portion 2016 of the inner sheath 2014 is positioned distal to a distal end, or pusher tip 2018, of the pusher shaft 2010. In the delivery position, the distal end portion 2016 of the inner sheath 2014 forms an inner cavity that can contain a compressed prosthetic valve 1500. In the retracted position, the distal end 2017 of the inner sheath 2014 is positioned proximal to or aligned axially with the pusher tip 2018. As the inner sheath 2014 moves from the delivery position toward the retracted position (either by retracting the inner sheath 2014 proximally relative to the pusher shaft 2010 or advancing the pusher shaft distally relative to the inner sheath), the pusher tip 2018 can force the prosthetic valve 1500 out of the distal end portion 2016 of the inner sheath.

As shown in FIG. 21, the inner sheath 2014 comprises one or more longitudinally disposed slots 2028 extending proximally from a distal end 2017 of the inner sheath. These slots 2028 can allow ventricular anchors 1556 of a prosthetic valve 1500 contained within the inner sheath 2014 to extend radially outward from the compressed main body of the prosthetic valve while the main body is retained in the compressed state within the inner sheath. In the embodiment shown in FIG. 21, two slots 2028 are shown oriented on diametrically opposed sides of a longitudinal central axis of the inner sheath 2014. This embodiment corresponds to the prosthetic valve 1500, which comprises two opposed ventricular anchors 1556. In other embodiments, the inner sheath 2014 can comprise a different number of slots 2028, for example four slots, that correspond to the number and location of ventricular anchors on a selected prosthetic valve. In some embodiments, such as shown in FIG. 21, the proximal end portion 2020 of the each slot 2028 comprises a rounded opening that has a greater angular width than the rest of the slot.

An outer sheath 2036 is positioned concentrically around a portion of the inner sheath 2014 and is slidable axially relative to the inner sheath. The outer sheath 2036 can be positioned to cover at least a portion of the distal end portion 2016 of the inner sheath 2014. In such a covered position, the ventricular anchors (e.g., anchors 1556 of prosthetic valve 1500) can be contained between the inner and outer sheath. The outer sheath 2036 is in this covered position while the loaded delivery system 2000 is inserted through the body and into the left ventricle. The outer sheath 2036 can be retracted proximally relative to the sheath 2014 to uncover the slots 2028 and allow the ventricular anchors 1556 to spring outward through the slots in the inner sheath 2014 during deployment. Alternatively, the inner sheath 2014 can be advanced distally relative to the outer sheath 2036 to uncover the slots 2028. The inner sheath 2014 can then be retracted relative to the prosthetic valve 1500 to complete implantation of the valve 1500. Additional details of delivery system 2000 and other suitable delivery systems and methods are disclosed in the '292 application.

FIGS. 26-28C show an exemplary embodiment another funnel shaped crimping device 300. The device 300 comprises an annular wall defining an inner lumen that gradually decreases in diameter from an insertion end 302 to an outlet end 304. The lumen comprises a generally cylindrical portion 306 adjacent the insertion end 302, and a tapered portion 308 adjacent to the outlet end 304.

Figure 28A:
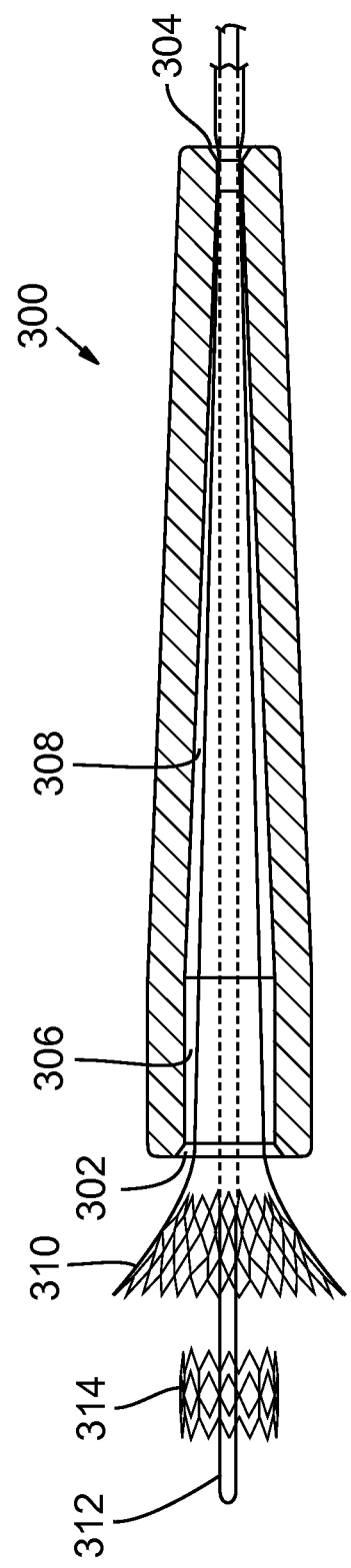
FIG. 28A is a cross-sectional side view of the crimping device of FIG. 26 with an exemplary catheter and tube sock positioned within the crimping device and an exemplary stent positioned around the catheter prior to crimping the stent.

As shown in FIGS. 28A-C, the device 300 is used to crimp an annular medical device (e.g., a stent 314 or a prosthetic heart valve) onto an elongated member (e.g. a catheter 312) using a tubular sock 310. The sock 310 can comprise a flexible, mesh-type fabric that provides low friction between the sock and the inner walls of the device 300. In some embodiments, the sock 310 can comprise polyethylene terephthalate (also known as PET or Dacron®). The sock 310 desirably is capable of expanding and contracting in diameter between at least the greatest diameter of the lumen and smallest diameter of the lumen, but has limited flexibility in the longitudinal direction such that longitudinal tension on the sock does not elongate the sock substantially. For example, in some embodiments the sock 310 comprises threads or strands running circumferentially around the sock that are resiliently stretchable, and threads or strands running longitudinally along the sock that are relatively less stretchable. Desirably, the sock 310 has a length that is greater than the length of the device 300, as shown in FIG. 28A.

To crimp the stent 314 onto the catheter 312, the catheter 312 and the sock 310 are positioned extending through the lumen of the device 300 with the catheter 312 positioned within the sock 310 and the stent positioned in the cylindrical portion 306 of the lumen in its radially expanded state, as shown in FIG. 28B. In some embodiments, the catheter 312 is first inserted into the sock 310, then the sock and catheter are inserted through the lumen of the device 300, and then the stent 314 is inserted into the cylindrical portion 306 of the lumen between the sock and the catheter. In other embodiments, the steps used to arrive at the configuration shown in FIG. 28 can be performed in a different order.

In some embodiments, the cylindrical portion 306 of the lumen has a slightly larger diameter than the diameter of the stent 314 in its radially expanded state. In other embodiments, the diameter of the cylindrical portion 306 can be smaller than the maximum diameter of the stent 314 in its radially expanded state, such that the stent is partially crimped when it is in the cylindrical portion 306. The stent can be partially crimped by another device before loading it into the cylindrical portion 306. The insertion end 302 of the device 300 can be beveled or chamfered around the edge of the lumen to help guide the stent 314 into the cylindrical portion 306. In the configuration of FIG. 28B, the stent 314 can be positioned on the catheter 312 at a desired longitudinal position relative to the catheter where it is desired that the stent be located after the stent is crimped onto the catheter.

The device 300 can then be moved longitudinally relative to the stent 314 such that the stent travels through the lumen through the tapered portion 308 and out through the outlet end 304 of the device, as shown in FIG. 28C. In some embodiments, the stent 314 can be held in one position while the device 300 is moved over the stent. For example, the portions of the sock 310 and/or the catheter 312 that extend from the outlet end 304 of the lumen can be gripped and held while the device 300 is forced to the left in FIG. 28B, moving the tapered portion 308 of the lumen over the stent 314. In other embodiments, the device 300 can be held in one position while the stent 314 is moved through the lumen. For example, the portions of the sock 310 and/or the catheter 312 that extend from the outlet end 304 of the lumen can be gripped and pulled to the right in FIG. 28B while the device 300 is held still, pulling the stent 314 and catheter 312 and sock 310 in unison through the tapered portion 308 and out of through the outlet end 304, as shown in FIG. 28C.

The sock 310 can have a first coefficient of friction against the stent 314 that is greater than the coefficient of friction between the sock and inner surface of the lumen. This can help prevent the stent 314 from moving within the sock 310 as the sock slides along the inner surface of the lumen. In some embodiments, the outer surface of the sock 310 can comprise a different material than the inner surface of the sock to create or enhance a difference in friction. For example, the outer surface of the sock 310 can be coated with a low-friction material, such as polytetrafluoroethylene (also known as PTFE or Teflon®). The inner surface of the lumen can also be coated with a low-friction material.

The minimal inner diameter of the lumen adjacent the outlet end 304 determines the crimped diameter of the stent after it exits the device 300, although in some embodiments the stent 314 can re-expand or recoil a small amount after the crimping forces are released. The slope of the tapered portion 308 between the maximum inner diameter at the cylindrical portion 306 and the minimal inner diameter adjacent the outlet end 304 can be selected to provide a desired mechanical advantage in converting the longitudinal forces into a radial crimping force. In some embodiments, the slope of the tapered portion 308 can vary along its length, such as have a more gradual taper adjacent to the cylindrical portion 306 and a steeper taper adjacent to the outlet end 304, or vice versa. As the stent slowly advances down the tapered portion 308, the device 300 converts the net longitudinal force between the device 300 and the stent 314 into a radially crimping force that crimps the stent onto the catheter 312. The sock 310 can shrink in diameter around the stent without bunching as the stent gradually becomes crimped moving through the tapered portion 308.

After the stent 314 exits the outlet end 304 of the device 300, the sock 310 is removed from the stent and the catheter 312. The sock 310 can be reused to crimp another stent in the device 300. With the stent crimped onto the catheter, the assembly can be ready for introduction into the body.

The sock 310 can prevent the device 300 from scratching or damaging the stent 314. Furthermore, the sock 310 can distribute the longitudinal forces over the whole outer surface of the stent instead of concentrating the longitudinal forces on one end of the stent, which would be the case if the stent were pushed through the lumen with a plunger device. Pulling the stent with the sock rather than pushing the stent with a plunger can also reduce longitudinally compressive forces on the stent, which can damage the stent and can tend to cause the stent to want to expand radially, and can reduce damage to the leading end of the stent related to the leading end of the stent catching on the inner surfaces of the device 300.

In some embodiments, an assembly comprising the device 300, the catheter 312, the sock 310, and the stent or prosthetic valve 314 can be arranged in a pre-crimping configuration, such as shown in FIG. 28B, and then stored for later crimping. For example, the components can be manufactured and assembled in such a pre-crimping configuration and packaged in a sterile container, optionally filled with a fluid. A user can later open the sterile container in a sterile operating room just prior to implantation of the stent into the body, crimp the stent onto the catheter by moving the stent through the device 300, and then introduce the stent and catheter into the body.

The method of crimping a medical device using the crimping device 300 and the sock 310 as described above is particularly useful for crimping a medical device having a plastically expandable metal frame. However, the assembly could be adapted to compress a self-expandable medical device. When crimping a self-expandable medical device, the sock 310 can be used to pull the medical device outwardly through outlet 304 and into a delivery sheath of a delivery device.

FIGS. 29-35 show an exemplary embodiment of a crimping device 400 that comprises a plurality of rollers 406 for crimping a medical device. The device 400 comprises an outer shell 402 and an inner shell 404 that are rotatable relative to each other about a longitudinal axis, and a plurality of rollers 406 positioned within the inner shell 404.

The outer shell 402 is generally cylindrical and comprises an end plate 408 at either end. The end plates 408 each comprise a plurality of slots 412 disposed around a central opening 414. In the embodiment shown, the slots 412 are generally arcuate, or banana shaped, though the shape of the slots 412 can vary in other embodiments. The number of the slots 412 in each end plate 408 is equal to the number of rollers 406 that are present, which is four in the illustrated embodiment. The outer shell 402 can optionally include a lateral opening 422 between the two end plates 408 to allow access to the inner shell 404.

The inner shell 404 is also generally cylindrical, but slightly smaller in dimension that the outer shell 402 such that the inner shell fits within the outer shell with enough room such that the inner and outer shells can rotate relative to one another about the longitudinal axis. The inner shell 404 comprises an end plate 410 at either end. Each end plate 410 comprises a plurality of radially extending slots 416 disposed around a central opening 418. The central opening 418 can be about the same diameter as the central opening 414 and the central openings 414, 418 can be aligned with each other, as shown in FIG. 32. The inner shell 404 can further comprise one or more openings 424 between the end plates 410 that allow access to the rollers 406.

FIG. 31 shows the crimping device 400 with the cylindrical portions of the inner and outer shells 402, 404 removed for purposes of illustration. In the embodiment shown, the four rollers 406 each comprise a pin 420 that extends longitudinally through the roller and protrudes out either longitudinal end of the roller into the end plates 408, 410. Each end of each pin 420 extends through one of the radial slots 416 in an inner end plate 410 and one of the arcuate slots 412 in an outer end plate 408.

As shown in FIGS. 31, 33 and 35, the rollers 406 each comprise a series of circular, disk-shaped elements 434 (referred to as disks) positioned along the pin. Each disk 434 is about the same diameter and the same thickness. Each disk 434 is spaced apart from the adjacent disk(s) by a gap having a width that is about the same as, or slightly greater than, the thickness of the disks. The width of the gaps can be selected based on the geometry of the stent being compressed. For example, the width of the gaps can be sufficiently small to prevent portions of the stent from moving into the gaps when the stent is being compressed. The disks 434 can be comprised of a fairly rigid material, such as a polymeric or metallic material, and can be coated with another material, such a coating that provides lower or higher friction with between the disks and between the disks and a stent, or a coating that reduces scratching damage caused by the disks contacting a stent.

In the embodiment shown in FIGS. 29-35, the device 400 has four rollers 406a, 406b, 406c, and 406d that are oriented parallel to one another and spaced evenly around the longitudinal center axis of the device. The four rollers 406 are constrained by the radial slots 416 such that the rollers can move radially inwardly and outwardly relative to the center axis, but the four rollers 406 maintain their equal circumferential spacing. The disks 434 of each roller 406 can be positioned partially within the gaps between the disks of the adjacent rollers, as shown in FIGS. 33 and 35. It is therefore desirable for the device 400 to have an even number of rollers 406, such as four, six or eight rollers, such that each opposing pair of rollers can be symmetrical about the center axis while each roller is offset from the two rollers adjacent to it. In the illustrated embodiment, opposing rollers 406a and 406c are symmetric about the center axis and opposing rollers 406b and 406d are symmetric about the center axis, but the disks 434a, 434c of the rollers 406a, 406c are longitudinally offset from the disks 434b, 434d of the rollers 406b, 406d by about the width of one of the disks. This offset allows the disks 434a and 434c to move into the gaps between the disks 434b and 434d, and vice versa, when the four rollers 406 moved toward the radially contracted configuration shown in FIGS. 31, 34 and 35.

FIGS. 32 and 33 show the device 400 in a radially expanded configuration. In this state, the pins 420 are positioned at the radially outer ends of the radial slots 416 and at respective first ends of the arcuate slots 412, and the disks 434 of each roller are spaced apart from the disks of the adjacent rollers. In other embodiments, the disks 434 can remain partially positioned in the gaps between the disks of the adjacent rollers even in the fully radially expanded state, such that the rollers are never spaced apart from the adjacent rollers.

The end view of FIG. 32 illustrates that, in the radially expanded configuration, the crimping device 400 has an open cylindrical region extending through the device from the central opening 414 in the end plate 408 at one end of the device 400 to the central opening 414 in the opposing end plate 408 at the other end of the device. The open region allows for a compressible annular device 430 (e.g. a stent or prosthetic valve) to be inserted through the central openings 414, 418 at one end of the device and into the open region between the four rollers 406. In the example of FIG. 32, the stent 430 is positioned around a central catheter 432 within the four rollers 406.

In order to crimp the stent 430 onto the catheter 432, the rollers 406 are moved radially inwardly in unison, with the outer surfaces of the disks 434 contacting the stent and applying compressing pressure on the stent until the stent is radially compressed to a desired crimped diameter, as shown in FIG. 34.

In order to cause the rollers 406 to move radially inwardly and compress the stent 430, the inner shell 404 and the outer shell 402 are rotated relative to one another about the center axis. The outer end plates 408 are fixed to the outer shell 402 and rotate with the outer shell, while the inner end plates 410 are fixed to the inner shell 404 and rotate with the inner shell. As the outer shell 402 and outer end plates 408 rotate (clockwise in the view of FIG. 32) relative to the inner shell 404 and inner end plates 410, the arcuate slots 412 force the pins 420 to move radially inwardly as the pins 420 move along the arcuate slots from the first ends of the arcuate slots (as shown in FIG. 32) toward the middle of the arcuate slots (as shown in FIG. 34). When the pins 420 are positioned at the portion of the arcuate slots that are closest to the center axis, the rollers 406 are positioned at their closest position to the center axis and the medical device 430 is radially compressed around the catheter 432. As rollers 406 move radially inwardly, the disks approach the disks of the adjacent rollers and enter the gaps therebetween such that the pins 420 can continue to move radially inwardly to the maximally radially contracted configuration of FIGS. 34 and 35.

Further rotation of the outer end plates 408 in the same direction (clockwise in FIGS. 32 and 34) relative to the inner end plates 410 causes the pins 420 to move toward the other ends of the arcuate slots 412, which causes the pins 420 to move radially outwardly along the radial slots 416 and causes the rollers 406 to move radially outwardly apart from each other back a radially expanded configuration that is equivalent to that shown in FIG. 32. At this point, the crimped medical device 430 (on catheter 432) can be removed from the crimping device 400 through openings 414, 418.

Variations of the crimping device 400 can be configured to crimp stents having various maximum and minimum diameters. For example, some exemplary stents have a pre-crimping diameter of up to 30 mm or more, and some exemplary stents have a post-crimping diameter of 1.8 mm or less. Some stents can have a difference of 20 mm or more between their pre-crimping diameter and their post-crimping diameter. To accommodate particular types of stents, the diameter of the disks 434, the depth of the gaps between the disks, and the length and radial positions of the slots 412 and 416 can be selected accordingly. For example, to accommodate a stent that has a smaller crimped diameter, then device 400 can be modified by increasing the diameter of the disks 434 or by moving the slots 412 and/or the slots 416 radially closer to the center axis, and the opposite modifications can be made for a stent that has a larger fully crimped diameter. In some embodiments, the outer end plates 408 and/or the inner end plates 410 can be swapped out to adjust the location of the slots 412 and 416. In some embodiments, the radial slots 416 can have a radial length that is longer than the actual radial travel of the pins 420, such that the inner end plates 410 do not need to be adjusted when the outer end plates 408 are adjusted to accommodate a different size of stent.

In some embodiments, the central openings 414, 418 can be sized to limit the size of the stent that can be inserted into the device 400. This can help prevent a stent that is too large from being inserted into the device 400 and possibly damaging the device 400 or the stent. In other embodiments, the outer central opening 414 is sized to limit diameter of stents that can be inserted into the device 400, while the inner central opening 418 has a maximum diameter that is large enough to accommodate the largest diameter of stent that the rest of the device 400 can be used with.

Figure 36:
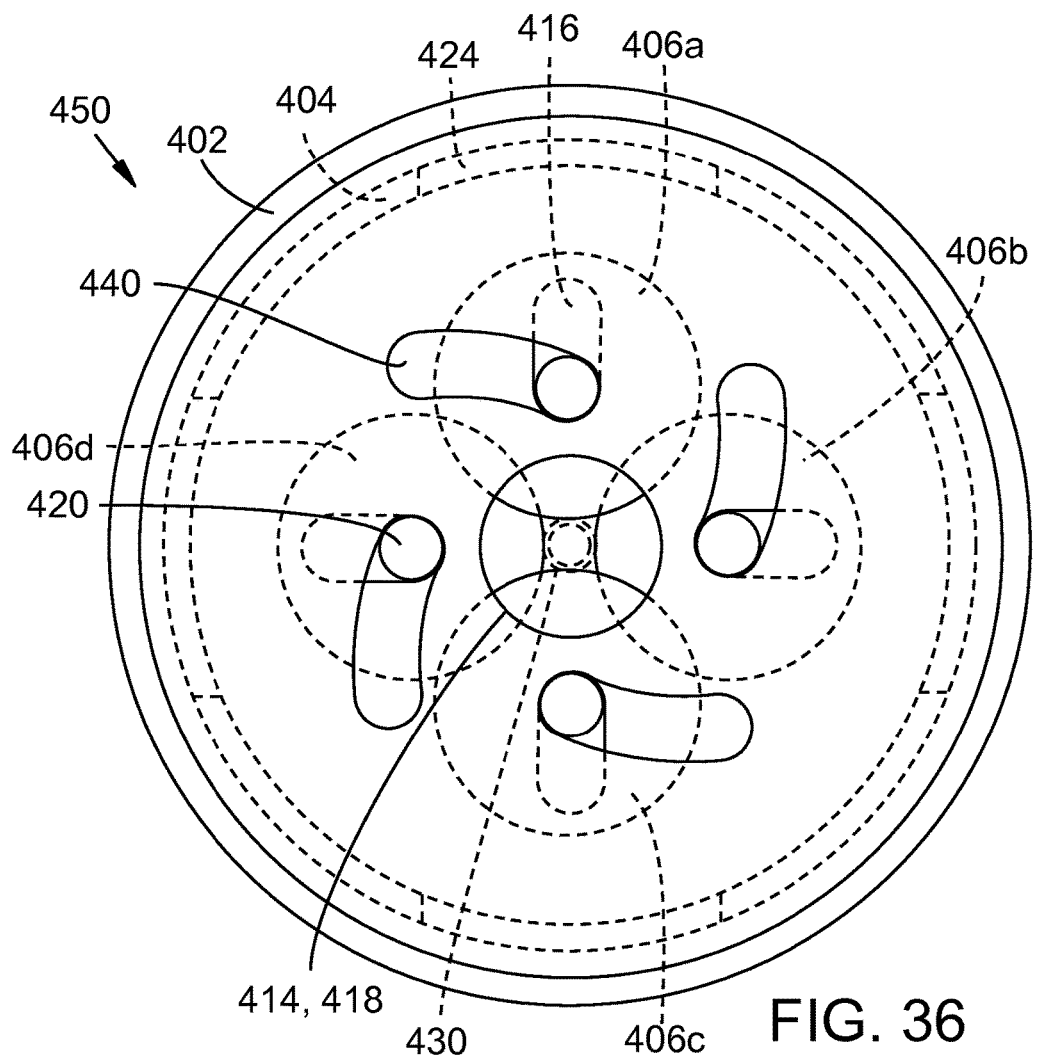
FIG. 36 is an end view of an alternative embodiment of the crimping device of FIG. 29.

The slots 412 can be any length or shape, straight or arcuate, and when arcuate, the slots 412 can be concave toward the outer perimeter of the device 400 (as in the embodiment 400) or concave toward the center axis of the device. For example, in an alternative embodiment 450 shown in FIG. 36 the slots 440 in the outer end plates are arcuate and concave toward the center axis. In other embodiments, the slots in the outer end plates can be straight. Assuming that the slots 416 in the inner end plates 410 are straight radial slots, the slots in the outer end plates can have any orientation as long as they have some variation in the radial dimensions along the length of the slot and also have some variation the circumferential dimension along the length of the slots. It will be appreciated that in alternative embodiments the outer end plates can comprise the straight radial slots while the inner end plates comprise the sloped slots.

The "slope" of the slots in the outer end plate determines the mechanical advantage in transferring a net rotational force between the outer and inner shells 402, 404 into radial forces on the rollers 406. The slope of the slots at any given point along the length of the slot is defined as the ratio of the change in the radial dimension to the change in the circumferential dimension. The slope of the slots can change along the length of the slots. For example, in the example of the arcuate slots 412, the slope is approximately zero in the middle of the slots (where the pins 420 are located in FIG. 34) and the slope gradually increases toward either end of the slot. A smaller slope provides greater mechanical advantage and a greater slope provides less mechanical advantage.

The slope of the slots in the outer end plates is also related to the rate of motion of the rollers 406. A greater slot slope corresponds to a relatively high rate of crimping motion (i.e., movement of the rollers 406 in the radial direction) for a given net rotational motion between the inner and outer shells, while a smaller slot slope corresponds to a relatively low rate of crimping motion for the same net rotational motion between the inner and outer shells. Thus, the slop of the slots in the outer end plates can be selected to achieve a desired amount of control of the crimping motion of the rollers 406. In the exemplary embodiment of FIGS. 29-35, the arcuate slots 412 decrease in slope from the ends of the slots toward the middle of the slots. As the crimping process of the device 400 proceeds from the configuration of FIGS. 32 and 33 toward the configuration of FIGS. 34 and 35, the pins 420 initially travel along the high slope portion of the slots 412, resulting in a relatively low mechanical advantage and a relatively high rate of motion of the rollers 406 in the radially inward direction. This can be appropriate for the initial crimping of a stent where relatively lower radial force and relatively lower crimping finesse is required. However, as the crimping process proceeds, the slope of the slots 412 where the pins 420 are located decreases, resulting in a relatively high mechanical advantage and a relatively lower rate of motion of the rollers 406 in the radially inward direction. This can be appropriate for the final crimping stages where relatively higher radial force is needed to compress the stent and greater crimping finesse is required to ensure that the stent is accurately compressed to a desired minimum diameter. Furthermore, with the arcuate slots 412, subsequent net rotation between the inner and outer shells in the same direction causes the pins 420 to move past the middle point of the slots 420 and toward the other end of the slots, allowing the rollers to move back radially outwardly away from the crimped stent.

In other embodiments, the slots in the outer end plates can have various other slope profiles. For example, in the embodiment shown in FIG. 36, the slope of the slots 440 is lower in when the rollers are in the radially expanded position and the slope of the slots 440 gradually increases toward a maximum slope as the rollers move radially inwardly toward the fully crimped position shown in FIG. 36. This results in more finesse and mechanical advantage during the initial crimping stages and less finesse and mechanical advantage during the final crimping stages, which can be desirable for crimping certain types of objects. In other embodiments, the slots in the outer end plates can have a constant slope.

The outer shell 402 and the inner shell 404 can be rotated relative to each other in various manners to cause the crimping motion. For example, the inner and outer shells can be manually rotated relative to each other by an operator directly applying a rotational force to one or both of the inner and outer shells. In other embodiments, the relative rotation between the inner and outer shells can be automated. When manual or automated, the rate of the relative rotation can be carefully controlled throughout the crimping process to provide a desired rate crimping. In some embodiments, the inner shell 404 can be held still while the outer shell 402 is rotated, and in other embodiments, the outer shell can be held still (such as fixed to a table or support) while the inner shell is rotated. The opening 422 in the outer shell 402 (see FIG. 29) can provide access to the inner shell 402 for applying rotational force to the inner shell and/or can provide a gripping location for applying rotational force to the outer shell. The openings 424 in the inner shell 404 can provide a gripping location of the inner shell for applying a rotational force. In other embodiments, additional components, such as a lever or handle, can be attached to one or both of the shells 402, 404 to facilitate applying rotational forces. In some embodiments, at least one of the outer end plates can comprise a circumferential slot of other opening that allows a lever or handle attached to the inner shell or inner end plate to protrude longitudinally out through the outer end plate. In some embodiments, a handle or lever attached to the cylindrical portion of the inner shell 404 can protrude radially out through the opening 422 in the outer shell 402.

In addition to each roller 406 moving radially inwardly and outwardly in response to the relative rotation between the inner and outer shells 402, 404, each roller 406 can also be rotated about the center axis of its respective pin 420 during the crimping process. All of the rollers 406 rotate in the same direction, either clockwise or counterclockwise in the view of FIGS. 32 and 34. When the rollers 406 are in contact with the stent 430, the rotation of the rollers causes the stent and/or the catheter 432 to rotate about the center axis of the device 400, but in the opposite direction of the rollers. For example, if the rollers are rotating in the clockwise direction in FIG. 34, the stent 430 and/or the catheter 432 rotate in the counterclockwise direction. Desirably, all of the rollers rotate at the same speed (i.e., the perimeter surfaces of the disks 434 move circumferentially at the same speed), such that they can all contact the rotating stent 430 without slipping.

The rotation of the rollers 406 and the stent 430 during the crimping process helps reduce damage to the stent caused by the contact by the roller, such as scratching and denting, especially when the disks 434 are comprised of a relatively hard material. The rotation of the rollers 406 allows the radial crimping forces from the rollers on the stent to be distributed around the outer surface of the stent rather than being concentrated at the discrete locations where the rollers contact the stent. Desirably, the rotational speed of the four rollers 406 is sufficiently great such that the stent makes at least ¼ of a rotation during the crimping process, such that the rollers contact the outer surface of the stent around its whole circumference during the crimping process. It can be further desirable for the rotational speed of the rollers 406 to be sufficiently great such that the stent makes at least one full rotation during the crimping process, such that each of the rollers contacts the outer surface of the stent around its whole circumference during the crimping process. It can be even further desirable for the rotational speed of the four rollers 406 to be sufficiently great such that the stent makes plural full rotations during the crimping process, such that the crimping forces are more evenly distributed around the circumference of the stent during the crimping process.

In order to cause the rollers 406 to rotate, rotational forces can be applied to at least one end of each of the pins 420. This can be accomplished in any number of manners. In some embodiments (not shown), the pins 420 project out past the outer end plate at one or both ends of the device 420 and a drive belt or drive chain is coupled around all of the pins to cause them to rotate in the same direction at the same rotational speed. The drive belt or drive chain can be driven by a motor or other drive mechanism.

In some embodiments, rotation of the rollers 406 can be caused by an engagement between the pins 420 and the inner surfaces of the sloped slots (e.g., 412 or 440). The pins 420 can be engaged with the inner surfaces of the sloped slots in such a way that there is no slippage between the engaged contact surfaces and the pin is caused to roll along the inner surface of the slot as the pin translates along the slot. In these embodiments, the rotation of the rollers 406 is caused by, and is function of, the relative rotation between the outer and inner shells 402, 404. By linking the rotation of the rollers to the radial translation of the rollers, an independent drive source is not needed to rotate the roller. In addition, the number of rotations each roller makes, and the number of rotations the stent makes, during the crimping process can be specifically selected and controlled by engaging the pins with the inner surfaces of the sloped slots.

The pins can be engaged with the inner surfaces of the sloped slots using various techniques and/or mechanisms. In some embodiments, there is sufficient friction between the pins and the inner surfaces of the sloped slots to prevent any sliding between the contacting surfaces and force the pins to roll along the slots. In other embodiments, each of the pins can comprise a plurality of teeth or cogs around the circumference of the pin at the portion of the pin that is positioned within a sloped slot, and the inner surfaces of the sloped slots can comprise corresponding teeth that mesh with the teeth on the pins to prevent sliding between the contact surfaces and force the pins to roll along the slots. FIGS. 37 and 38 show examples of such embodiments.

Figure 37A:
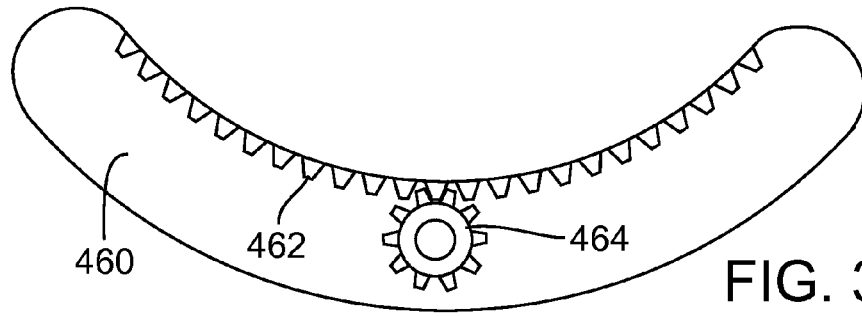
FIGS. 37A, 37B, 38A and 38B show an alternative configuration for an interface between roller pins and sloped slots of the crimping device of FIG. 29.

In FIG. 37A, an exemplary sloped slot 460 comprises a row of teeth 462 only on the radially outer surface of the slot and a geared pin 464 that rolls along the teeth 462. In this embodiment, the geared pin 464 is kept urged against the teeth 462 on the radially outer surface of the slot 460 while the geared pin 464 rolls along the slot. When a stent is being compressed by the rollers, the stent can exert a radially outward force on the rollers 406 that in turn causes the geared pins 464 to be urged radially outwardly against the teeth 464. In some of these embodiments, the geared pins 464 can remain engaged with the teeth 464 even after the stent is compressed and the rollers are moving radially outwardly away from the compressed stent and there is no longer a radially outward force on the rollers. For example, the device can include biasing mechanisms, such as springs, that maintain radially outwardly biasing forces on the rollers and pins.

Figure 37B:
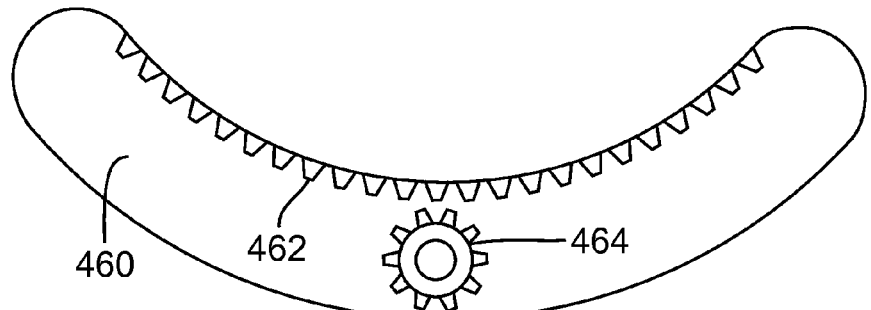

Causing the rollers 406 to rotate is not necessary when the rollers are disengaged from the stent after the stent is compressed. Thus, in alternative embodiments, as shown in FIG. 37B, the geared pin 464 can disengage from the teeth 462 when the rollers are moving radially outward such that the pins can slide along the slots without having to roll and the rollers are no longer forced to rotate as a function of the motion of the pins along the slots. As shown in FIG. 37B, the geared pin 464 can move radially away from the teeth 464 to provide the disengagement, or in some embodiments (not shown), the teeth 464 and the geared pins 464 can be configured to allow the rollers to "free spool" or "freewheel" when moving radially outwardly, such as by providing a clutch or other one-way ratcheting mechanism in the geared pin 464.

Figure 38A:
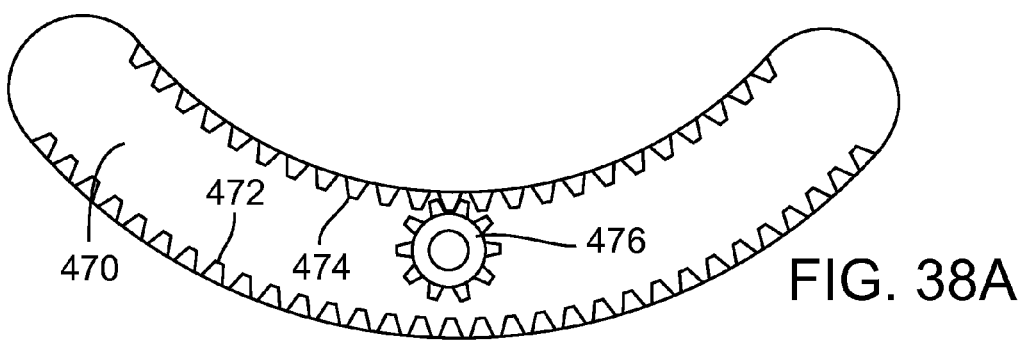
Figure 38B:
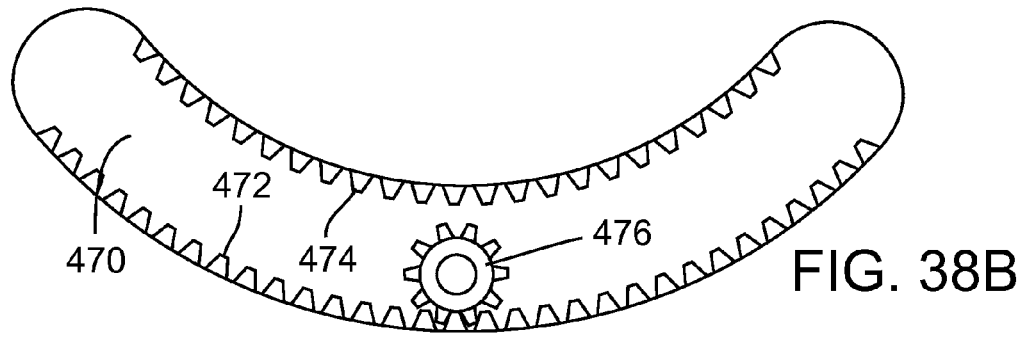

FIGS. 38A and 38B show another exemplary sloped slot 470 that comprises teeth 472 on the radially inner surface of the slot as well as teeth 474 on the radially outer surface of the slot. A geared pin 476 can be engaged with the teeth 474 on the outer side of the slot 470 when the rollers 406 are moving radially inwardly to compress a stent, and the geared pin 476 can transition to rolling along the teeth 472 on the inner side of the slot when the rollers are moving radially outwardly. A biasing mechanism can be provided to maintain a radially inward force on the pins such that, when there is no radially outward force on the rollers from a stent, the geared pins 476 are urged toward the teeth 472 on the radially inner sides of the slots 470.

Any of the presently disclosed crimping devices can be designed to apply forces such that it evenly reduces the diameter of the device being crimped. The crimping devices according to the present disclosure can be used to crimp any medical device that is expandable and compressible. Examples of such expandable medical devices include stented prosthetic heart valves, coronary stents, peripheral stents, other stented valves, venous valves, and stent grafts (e.g., endovascular grafts). Typically, medical devices such as prosthetic heart valves (e.g., prosthetic mitral or aortic heart valves) that are designed to be compressed for delivery (e.g., transcatheter delivery) are crimped to a smaller diameter prior to implantation in the body. The crimping devices according to the present disclosure can be used to crimp (e.g., reduce the radius of) any such device.

The size and proportions of the disclosed crimping devices can be adapted for and scaled to provide a suitable crimping device for any size medical device. In some embodiments, disclosed crimping devices can be optimized to crimp a device having a length of less than about 2 inches. In some embodiments, disclosed crimping devices can be optimized to crimp a device having a length of greater than about 2 inches. In some embodiments, disclosed crimping devices can be optimized to crimp a device having an expanded diameter of less than about 29 mm. In some embodiments, disclosed crimping devices can be optimized to crimp a device having an expanded diameter of greater than about 29 mm. In some embodiments, the crimping engagement surfaces can have a thickness that is approximately equal to the length of the device being crimped. For example, in some embodiments, the crimping engagement surfaces can contact substantially the entire length of the device being crimped. In some embodiments, the crimping engagement surfaces can have a thickness that is greater or less than the length of the device being crimped.

While the above embodiments have been described as being configured for crimping medical devices, the disclosed embodiments are not limited to such uses. Embodiments can be configured to hold a wide range of sizes of different parts in many different applications. For example, disclosed embodiments can be scaled up or down to hold or clamp any size of object, from very large to very small objects. Disclosed embodiments can also generally be used to crimp or crush any deformable object within the crimping jaws.

In view of the many possible embodiments to which the principles of the disclosure may be applied, it should be recognized that the illustrated embodiments are only preferred examples and should not be taken as limiting the scope of the disclosure. Rather, the scope of the disclosure is defined by the following claims. We therefore claim all that comes within the scope and spirit of these claims.

We claim:

1. A crimping device comprising:
an annular outer frame comprising a first axial end portion, a second axial end portion, and a central opening that defines a central axis extending through the central opening;
an inner frame extending through the central opening of the outer frame, the inner frame comprising a first axial end portion, a second axial end portion, and a plurality of jaw guides extending between the first axial end portion and the second axial end portion, wherein a radial distance from the central axis to the jaw guides increases moving axially along the inner frame from the first axial end portion toward the second axial end portion, and wherein the inner frame defines first and second openings at opposite ends of the inner frame and a central lumen extending axially through the inner frame from the first opening to the second opening and centered on the central axis; and
a plurality of jaws operatively coupled to the inner frame and the outer frame, each jaw positioned within a respective jaw guide of the inner frame,
wherein relative axial motion between the outer frame and the inner frame causes radial motion of the jaws for crimping a prosthetic device positioned within the central lumen of the inner frame,
wherein the crimping device is configured to be axially movable relative to a delivery catheter such that at least a portion of the delivery catheter can be inserted through the central lumen of the inner frame and can extend axially beyond the first and the second axial end portions of the outer and the inner frames, and
wherein at least one of the jaw guides of the inner frame comprises a closed slot having a first stop surface disposed adjacent the first axial end portion of the inner frame and a second stop surface disposed adjacent the second axial end portion of the inner frame, and wherein the jaws are operatively coupled to the inner frame such that the jaws are axially movable within the slot between the first and the second stop surfaces.

2. The crimping device of claim 1, wherein a radial position of the jaws varies as a function of an axial position of the inner frame relative to the outer frame.

3. The crimping device of claim 1, wherein relative axial motion between the outer frame and the inner frame causes engagement portions of the jaws to slide along the jaw guides.

4. The crimping device of claim 1, wherein inner portions of the jaws define an iris between said inner portions of said jaws and relative axial motion between the outer frame and the inner frame causes the iris to change in radial size.

5. The crimping device of claim 4, wherein the iris is fully contracted when the first axial end portion of the inner frame is adjacent to the jaws, and the iris is fully dilated when the second axial end portion of the inner frame is adjacent to the jaws.

6. The crimping device of claim 1, wherein a radial position of the jaws is based on the radial distance from the central axis to the jaw guides at an axial position where the jaws are engaged with the jaw guides.

7. The crimping device of claim 1, wherein relative axial motion between the outer frame and the inner frame causes the jaws to move radially in unison.

8. The crimping device of claim 1, wherein the crimping device is configured to transfer an axial force imparted on the inner frame into a radial compressive force imparted from inner portions of the jaws to a prosthetic device positioned between the jaws, wherein the axial force is proportional to the radial compressive force.

9. The crimping device of claim 8, wherein a mechanical advantage of the crimping device is a function of a slope of the jaw guides, the slope being a ratio of change in radial dimension to change in axial dimension.

10. The crimping device of claim 1, wherein the inner frame comprises a generally frustoconical shape.

11. The crimping device of claim 1, wherein the inner frame comprises an annular wall that extends angularly around the central opening of the inner frame and the jaw guides comprise respective closed slots extending radially through the wall.

12. The crimping device of claim 11, wherein an engagement portion of each jaw comprises a neck positioned within a respective one of the slots of the inner frame, the slots being narrower in angular width than portions of the jaws immediately adjacent to the neck.

13. The crimping device of claim 1, wherein the outer frame comprises a plurality of radially extending jaw support holes spaced angularly around the outer frame, an outer portion of each of the jaws being positioned at least partially within a respective one of the jaw support holes such that the jaws can move radially relative to the outer frame but are restricted from axial or angular motion relative to the outer frame.

14. The crimping device of claim 13, wherein relative axial motion between the outer frame and the inner frame causes the outer portions of the jaws to slide axially within the jaw support holes.

15. The crimping device of claim 1, in combination with a delivery catheter having an inflatable balloon positioned in the inner frame so that the prosthetic device can be crimped directly onto the balloon.

16. An assembly comprising:
a prosthetic device comprising a plastically-expandable metal frame;

a delivery catheter having an inflatable balloon portion; and a crimping device comprising:

an annular outer frame comprising a first axial end portion, a second axial end portion, and a central opening that defines a central axis extending through the central opening, an inner frame extending through the central opening of the outer frame, the inner frame comprising a first axial end portion, a second axial end portion, and a plurality of jaw guides extending between the first axial end portion and the second axial end portion, wherein a radial distance from the central axis to the jaw guides increases moving axially along the inner frame from the first axial end portion toward the second axial end portion, wherein the inner frame defines first and second openings at opposite ends of the inner frame and a lumen extending axially through the inner frame from the first opening to the second opening and centered on the central axis, and a plurality of jaws operatively coupled to the inner frame and the outer frame, each jaw positioned within a respective jaw guide of the inner frame, wherein the prosthetic device and the inflatable balloon portion of the delivery catheter are positioned in the lumen of the inner frame, and relative axial motion between the outer frame and the inner frame causes the jaws to move radially inwardly and crimp the prosthetic device onto the inflatable balloon portion, wherein the crimping device is movable along a length of the delivery catheter such that at least a portion of the delivery catheter extends through the first and the second axial end portions of the outer frame and extends through the first and second axial end portions of the inner frame, and wherein at least one of the jaw guides of the inner frame comprises a closed slot having a first stop surface disposed adjacent the first axial end portion of the inner frame and a second stop surface disposed adjacent the second axial end portion of the inner frame, and wherein the jaws are operatively coupled to the inner frame such that the jaws are axially movable within the slots between the first and the second stop surfaces.

* * * * *